United States Patent
Collado Cano et al.

(10) Patent No.: US 6,498,180 B1
(45) Date of Patent: Dec. 24, 2002

(54) EXCITATORY AMINO ACID RECEPTOR MODULATORS

(75) Inventors: Ivan Collado Cano, Madrid (ES); Concepcion Pedregal Tercero, Madrid (ES); Alicia Marcos Llorente, Las Rozas (ES); Beatriz Lopez de Uralde Garmendia, Madrid (ES); Maria Rosario Gonzalez Garcia, Madrid (ES); Ana Belen Bueno Melendo, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/979,322

(22) PCT Filed: May 26, 2000

(86) PCT No.: PCT/EP00/04903

§ 371 (c)(1),
(2), (4) Date: Nov. 16, 2001

(87) PCT Pub. No.: WO00/75101

PCT Pub. Date: Dec. 14, 2000

(30) Foreign Application Priority Data

Jun. 3, 1999 (EP) .............................. 99500090

(51) Int. Cl.⁷ ..................... C01D 311/90; A61K 31/35; A61P 25/28; C07C 229/28
(52) U.S. Cl. ..................... 514/381; 514/531; 548/253; 560/124
(58) Field of Search ................. 548/253; 514/381, 514/531; 560/124

(56) References Cited

FOREIGN PATENT DOCUMENTS

| EP | 0 870 760 | 10/1998 |
| JP | 06179643 | * 6/1994 |
| JP | 08 301825 | 11/1996 |
| WO | WO 97 19049 | 5/1997 |
| WO | WO 98 00391 | 1/1998 |

OTHER PUBLICATIONS

Pellicciari, Roberto, et al.: Synthesis and Pharmacological Characterization of All Sixteen Steroisomers of 2–(2'–Carboxy–3'–phenylcyclopropyl)glycine, *J. Med. Chem.* 39(11), pp. 2259–2269 (1996); XP002122695.

Shimamoto, Keiko, et al.: "Syntheses and Conformation Analyses of Glutamate Analogs: 2–(2–Carboxy–3–substituted–cyclopropyl)glycines as Useful Probes for Excitatory Amino Acid Receptors," *J. Med. Chem.* 39(2), pp. 407–423, XP002122696 (1996).

Mazon, Angel, et al.: "Enantioselective Synthesis of 2–(3'–Alkyl–2'–Carboxy Cyclopropyl) Glycines," *Tetrahedron* 55, pp. 7057–7065 (1999).

Shimamoto, Keiko, et al.: "Synthesis of Trans–3'–substitued–CCG–IV Analogs and Their Characterization to Ionotropic Glutamate Receptors," *Bioorg. Med. Chem. Lett.* 6(20), pp. 2381–2386 (1996).

Shimamoto, Keiko, et al.: "Sythesis of Four Diastereomeric L–2–(Carboxycyclopropyl)glycines. Conformationally Constrined L–Glutamate Analogues," *J. Org. Chem.* 56, pp. 4167–4176 (1991).

Wilsch, Volker W., et al.: "Metabotopic Glutamate Receptor Agonist DCG–IV as NMDA Receptor Agonist in Inmature Rat Hippocampal Neurons," *Eur. J. Pharmacol.* 262, pp. 287–291 (1994).

* cited by examiner

*Primary Examiner*—T. A. Solola
*Assistant Examiner*—Andrea D. Small
(74) *Attorney, Agent, or Firm*—Arvie J. Anderson

(57) ABSTRACT

Compounds of formula (I) in which $R^1$ is halo-$C_{1-10}$ alkyl; halo-$C_{2-10}$ alkenyl; or $(CH_2)_nY$ in which n is 1 or 2 and Y is OH, CN, $N_3$, $OR^3$, SH, $S(O)_pR^4$, $S(O)_3H$, $NH_2$, $NHR^5$, $NR^6R^7$, $NHCOR^8$, $NO_2$, $CO_2H$, $CONHR^9$, 1H-tetrazol-5-yl, 5-phenyltetrazol-2-yl or $PO_3H_2$; $R^3$, $R^5$, $R^6$, $R^7$, $R^8$ and $R^9$ are each selected independently from $C_{1-4}$ alkyl, aryl and aryl-$C_{1-4}$ alkyl; $R^4$ is selected from $C_{1-4}$ alkyl, aryl, aryl-$C_{1-4}$ alkyl, and 1H-tetrazol-5-yl, carboxy-(1–4C)alkyl and 1H-tetrazol-5-yl-$C_{1-4}$ alkyl; and p is 0, 1, 2 or 3; or a salt or ester thereof, provided that $R^1$ is not methoxymethyl, modulate metabotropic glutamate receptor function and are useful in treating disorders of the central nervous system.

12 Claims, No Drawings

EXCITATORY AMINO ACID RECEPTOR MODULATORS

This application is a U.S. national phase entry, prudent to 35 USC 371, of PCT/EP00/04903, filed May 26, 2000 and published on Dec. 14, 2000, International Publication No. WO 00/75101, which claims the benefit of European Application No. 99500090.8 filed Jun. 3, 1999.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Comas, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D or C, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and anti-emetic agents.

Pellicciari et al., *J. Med. Chem.*, 1996, 39, 2259–2269 refers to compounds known as metabotropic glutamate receptor agonists, in particular (2S,1'S,2'S)-2-(2-carboxycyclopropyl)glycine, also known as L-CCG-I; (2S, 1'S,2'R,3'R)-2-(2'-carboxy-3'-(methoxymethyl)cyclopropyl-glycine, also known as cis-MCG-I; (2S,1'S,2'R,3'S)-2-(2'-carboxy-3'-(methoxymethyl)cyclopropylglycine, also known as trans-MCG-I; and (2S,1'R,2'R,3'R)-2-(2',3'-dicarboxy-cyclopropyl)glycine, also known as DCG-IV. The paper also describes the synthesis of the sixteen possible stereoisomers of 2-(2'-carboxy-3'-phenylcyclopropyl) glycine and their evaluation as excitatory amino acid receptor ligands. The compound (2S,1'S,2'S,3'R)-2-(2'-carboxy-3'-phenylcyclopropyl)glycine, also known as PCCG 4 is reported to be a metabotropic glutamate receptor antagonist.

Japanese patent application publication number JP 06179643 discloses MCG and generically discloses (2S,1'S, 2'R)-2-(2-carboxy-3-alkoxymethyl- and 3-aralkoxymethyl-cyclopropyl)glycines as glutamate receptor agonists.

International patent application publication number WO 97/19049 discloses PCCG 4 and also generically discloses various 2-carboxy-3-arylcyclopropylglycines having affinity for metabotropic glutamate receptors.

International patent application publication number WO 98/00391 discloses 2-carboxy-3,3-dihalocyclopropylglycines, including (2S,1'S,2'S)-2-(2-carboxy-3,3-difluoro)-cyclopropylglycine as metabotropic glutamate receptor agonists.

European patent application, publication number EP-A1-0870760 discloses that certain 3-substituted 2-carboxycyclopropyl glycine derivatives are modulators of metabotropic glutamate receptor function. The preferred compounds are said to be those in which the substituents at the 1 and 2 positions are in a trans relationship. The examples illustrate such compounds in which the substituents at the 1 and 3 positions are also in a trans relationship. One such compound is (2S,1'S,2'S,3'S)-2'-carboxy-3'-methylcyclopropylglycine.

Surprisingly, novel 3-substituted 2-carboxycyclopropyl glycine derivatives have now been found which are potent agonists of glutamate at metabotropic glutamate receptors.

Accordingly, the present invention provides a compound of the formula:

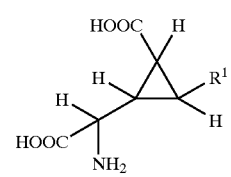

in which:

R$^1$ is halo-C$_{1-10}$ alkyl; halo-C$_{2-10}$ alkenyl; or (CH$_2$)$_n$Y in which n is 1 or 2 and Y is OH, CN, N$_3$, SH, S(O)$_p$R$^4$, S(O)$_3$H, NH$_2$, NHR$^5$, NR$^6$R$^7$, NHCOR$^8$, NO$_2$, CO$_2$H, CONHR$^9$, 1H-tetrazol-5-yl, 5-phenyltetrazol-2-yl, or PO$_3$H$_2$; R$^3$, R$^5$, R$^6$, R$^7$, R$^8$ and R$^9$ are each selected independently from C$_{1-4}$ alkyl, aryl and aryl-C$_{1-4}$ alkyl; R$^4$ is selected from C$_{1-4}$ alkyl, aryl, aryl-C$_{1-4}$ alkyl, 1H-tetrazol-5-yl, carboxy-C$_{1-4}$ alkyl and 1H-tetrazol-5-yl-C$_{1-4}$ alkyl; and p is 0, 1, 2 or 3;

or a salt or ester thereof.

Compounds of the invention have been found to be agonists of glutamate at metabotropic glutamate receptors and are therefore useful in the treatment of diseases of the central nervous system such as neurological diseases, for example neurodegenerative diseases, and as antipsychotic, anxiolytic, drug-withdrawal, antidepressant, anticonvulsant, analgesic and anti-emetic agents.

It will be appreciated that the compounds of formula (I) contain at least four asymmetric carbon atoms, three being in the cyclopropane ring and one being at the α-carbon of the amino acid group. Accordingly, the compounds of the invention may exist in and be isolated in enantiomerically pure form, in racemic form, or in a diastereoisomeric mixture.

Preferred compounds of the invention are those of the formula

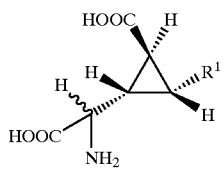

Ia

The amino acid moiety preferably has the natural amino configuration. Accordingly, preferred compounds according to the invention are those of the formula:

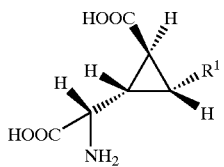

Ib

As used herein, the term halogen atom, as such or as halo, for example as in haloalkyl, includes a fluorine or chlorine atom; a $C_{1-10}$ alkyl group includes a $C_{1-4}$ alkyl group and can be straight or branched chain, such as, for example, methyl, ethyl, propyl, isopropyl, butyl and isobutyl, and is preferably methyl or ethyl. A $C_{2-10}$ alkenyl group includes, for example, vinyl, prop-2-enyl, but-3-enyl, pent-4-enyl and isopropenyl, and an alkenyl group can contain more than one double bond and, in addition, one or more triple bonds. A preferred alkenyl group is of the formula R'—CH=CH—$(CH_2)_r$— where R' is hydrogen or $C_{1-4}$ alkyl and r is 0, 1 or 2. An aryl group, as such or in an aryl-$C_{1-4}$ alkyl may be, for example, a phenyl group or a substituted phenyl group, for example with one or two substituents selected independently from halogen, $C_{1-4}$ alkyl and $C_{1-4}$ alkoxy. An example of an aryl group is phenyl or 3-chlorophenyl. An example of an aryl-$C_{1-4}$ alkyl group is benzyl.

A particular sub-group of compounds of formula I is that in which $R^4$ is selected from $C_{1-4}$ alkyl, aryl, aryl-$C_{1-4}$ alkyl and 1H-tetrazol-5-yl-$C_{1-4}$ alkyl.

Examples of particular values for $R^1$ are: for a halo-$C_{1-10}$ alkyl group: fluoromethyl; trifluoromethyl; 2-fluoroethyl; trifluorethyl, such as 2,2,2-trifluoroethyl; chloromethyl; 2-chloroethyl; trichloromethyl; and trichloroethyl, such as 2,2,2-trichloroethyl; for a halo-$C_{2-10}$ alkenyl group: 2-fluorovinyl and 2,2-difluorovinyl; for a $(CH_2)_nY$ group: hydroxymethyl, 2-hydroxyethyl, 2-benzyloxyethyl, cyanomethyl, 2-cyanoethyl, azidomethyl, 2-azidoethyl, 2-methoxyethyl, mercaptomethyl; 2-mercaptoethyl, methanethiomethyl, 2-methanethioethyl, 1H-tetrazol-5-ylthiomethyl, carboxymethylthiomethyl, phenylthiomethyl, methanesulfinylmethyl, 2-methanesulfinylethyl, methanesulfonylmethyl, phenylsulfinylmethyl, phenylsulfonylmethyl, 2-methanesulfonylethyl, 2-phenylthioethyl, 2-benzylthioethyl, aminomethyl, acetylaminomethyl, benzoylaminomethyl, 3-chlorobenzoylaminomethyl, benzylamidomethyl, methylaminomethyl, nitromethyl, 2-nitroethyl, 1H-tetrazol-5-ylmethyl, 2-(1H-tetrazol-5-yl)ethyl, 5-phenyltetrazol-2-ylmethyl, carboxymethyl, 2-carboxyethyl, aminocarbonylmethyl, phosphonomethyl, acetamidomethyl, benzamidomethyl and 2-benzamidoethyl.

Examples of particular values for $R^3$, $R^5$, $R^6$, $R^7$, $R^8$ and $R^9$ are:
for a $C_{1-4}$ alkyl group: methyl or ethyl;
for an aryl group: phenyl or 3-chlorophenyl; and for an aryl-$C_{1-4}$ alkyl group: benzyl.

Examples of particular values for $R^4$ are:
for a $C_{1-4}$ alkyl group: methyl;
for an aryl group: phenyl;
for an aryl-$C_{1-4}$ alkyl group: benzyl;
for a carboxy-$C_{1-4}$ alkyl group: carboxymethyl; and
for a 1H-tetrazol-5-yl-$C_{1-4}$ alkyl group: 1H-tetrazol-5-ylmethyl.

Preferably $R^1$ is selected from fluoromethyl, trifluoromethyl, 2-fluoroethyl, 2,2,2-trifluoroethyl, chloromethyl, 2-chloroethyl, trichloromethyl, 2,2,2-trichloroethyl, 2-fluorovinyl, 2,2-difluorovinyl, hydroxymethyl, 2-hydroxyethyl, 2-benzyloxyethyl, cyanomethyl, 2-cyanoethyl, azidomethyl, 2-azidoethyl, mercaptomethyl, 2-mercaptoethyl, methanethiomethyl, 2-methanethioethyl, 1H-tetrazol-5-ylthiomethyl, carboxymethylthiomethyl, phenylthiomethyl, methanesulfinylmethyl, 2-methanesulfinylethyl, methanesulfonylmethyl, phenylsulfinylmethyl, phenylsulfonylmethyl, 2-methanesulfonylethyl, 2-phenylthioethyl, 2-benzylthioethyl, aminomethyl, acetylaminomethyl, benzoylaminomethyl, 3-chlorobenzoylaminomethyl, benzylamidomethyl, methylaminomethyl, nitromethyl, 2-nitroethyl, 1H-tetrazol-5-ylmethyl, 2-(1H-tetrazol-5-yl)ethyl, 5-phenyltetrazol-2-ylmethyl, carboxymethyl, 2-carboxyethyl, aminocarbonylmethyl, phosphonomethyl, acetamidomethyl, benzamidomethyl, and 2-benzamidoethyl.

A particular sub-group of compounds of formula I is that in which $R^1$ is selected from fluoromethyl, 2-fluoroethyl, trifluoromethyl, trichloromethyl, trichloroethyl, 2-trichloroethyl, 2-fluorovinyl, 2,2-difluorovinyl, hydroxymethyl, cyanomethyl, 2-cyanoethyl, azidomethyl, 2-azidoethyl, 2-benzyloxyethyl, mercaptomethyl, methanethiomethyl, 2-methanethioethyl, 1H-tetrazol-5-ylthiomethyl, methanesulfinylmethyl, 2-methanesulfinylethyl, methanesulfonylmethyl, 2-methanesulfonylethyl, aminomethyl, acetylaminomethyl, nitromethyl, 1H-tetrazol-5-ylmethyl, aminocarbonylmethyl, phosphonomethyl, acetamidomethyl and benzamidomethyl. Especially preferred are compounds in which $R^1$ is hydroxymethyl.

Particularly preferred compounds are:

(2SR,1'SR,2'RS,3'RS)-2-(3'-hydroxymethyl-2'-carboxycyclopropyl)glycine;
(2SR,1'SR,2'SR,3'RS)-2-[(3'-(2"-hydroxyethyl)-2'-carboxy)cyclopropyl]glycine;
(2SR,1'RS,2'RS,3'RS)-2-[3'-mercaptomethyl-2'-carboxycyclopropyl]glycine;
(2SR,1'RS,2'RS,3'RS)-2-[3'-carboxymethylthiomethyl-2'-carboxycyclopropyl]glycine;
(2SR,1'RS,2'RS,3'RS)-2-[3'-(1H-tetrazol-5-ylthiomethyl)-2'-carboxycyclopropyl]glycine;
(2SR,1'SR,2'SR,3'RS)-2-[(3'-(2"-mercaptoethyl)-2'-carboxy)cyclopropyl]glycine;

(2SR,1'RS,2'RS,3'RS)-2-[3'-methylthiomethyl-2'-carboxycyclopropyl]glycine;
(2SR,1'RS,2'RS,3'RS)-2-[3'-phenylthiomethyl-2'-carboxycyclopropyl]glycine;
(2SR,1'SR,2'SR,3'RS)-2-[(3'-(2"-phenylthioethyl)-2'-carboxycyclopropyl]glycine;
(2SR,1'SR,2'SR,3'RS)-2-[(3'-(2"-benzylthioethyl)-2'-carboxycyclopropyl]glycine;
(2SR,1'RS,2'RS,3'RS)-2-[3'-methylsulfonylmethyl-2'-carboxycyclopropyl]glycine;
(2SR,1'RS,2'RS,3'RS)-2-[3'-phenylsulfonylmethyl-2'-carboxycyclopropyl]glycine;
(2SR,1'SR,2'SR,3'RS)-2-[3'-azidomethyl-2'-carboxycyclopropyl]glycine;
(2SR,1'SR,2'SR,3'RS)-2-[(3'-(2"-fluoroethyl)-2'-carboxycyclopropyl]glycine;
(2SR,1'SR,2'SR,3'RS)-2-[(3'-(2"-chloroethyl)-2'-carboxycyclopropyl]glycine;
(2SR,1'SR,2'SR,3'RS)-2-[3'-acetylaminomethyl-2'-carboxycyclopropyl]glycine;
(2SR,1'SR,2'SR,3'RS)-2-[3'-benzoylaminomethyl-2'-carboxycyclopropyl]glycine;
(2SR,1'SR,2'SR,3'RS)-2-[3'-aminomethyl-2'-carboxycyclopropyl]glycine;
(2SR,1'SR,2'SR,3'RS)-2-[3'-benzylcarbonylaminomethyl-2'-carboxycyclopropyl]glycine;
(2SR,1'SR,2'SR,3'RS)-2-[3'-(m-chlorobenzoyl)aminomethyl-2'-carboxycyclopropyl]glycine;
(2SR,1'SR,2'SR,3'RS)-2-[3'-methylaminomethyl-2'-carboxycyclopropyl]glycine;
(2SR,1'RS,2'RS,3'RS)-2-[3'-trifluoromethyl-2'-carboxycyclopropyl]glycine;
(2SR,1'SR,2'SR,3'RS)-2-[(3'-(2"-(1H-tetrazol-5-yl)ethyl)-2'-carboxycyclopropyl]glycine;
(2SR,1'SR,2'SR,3'RS)-2-[(3'-(2"-azidoethyl)-2'-carboxycyclopropyl]glycine;
(2SR,1'SR,2'SR,3'RS)-2-[(3'-(2"-nitroethyl)-2'-carboxycyclopropyl]glycine;
(2SR,1'SR,2'SR,3'RS)-2-[(3'-(2"-benzyloxyethyl)-2'-carboxycyclopropyl]glycine;
(2SR,1'SR,2'SR,3'RS)-2-[3'-(5-phenyltetrazol-2-yl)methyl-2'-carboxycyclopropyl]glycine, and pharmaceutically acceptable salts and esters thereof.

A compound of especial interest is: (2S,1'S,2'R,3'R)-2-(3'-hydroxymethyl-2'-carboxycyclopropyl)glycine, as well as the pharmaceutically acceptable salts thereof.

This compound has been found to be highly potent as an agonist of glutamate at Group II metabotropic glutamate receptors (mGluR2 and mGluR3). It is believed to be the most highly potent 2'-carboxycyclopropyl)glycine (CCG) compound made to date.

The present invention includes salts of the formula (I) compounds. These salts can exist in conjunction with the acidic or basic portion of the molecule and can exist as acid addition, primary, secondary, tertiary, or quaternary ammnonium, alkali metal, or alkaline earth metal salts. Generally, the acid addition salts are prepared by the reaction of an acid with a compound of formula (I). The alkali metal and alkaline earth metal salts are generally prepared by the reaction of the hydroxide form of the desired metal salt with a compound of formula (I).

The salts of the compounds of formula I may be pharmaceutically-acceptable salts. However, other salts are included in the invention. They may serve as intermediates in the purification of compounds or in the preparation of other, for example pharmaceutically-acceptable, acid addition salts, or are useful for identification, characterisation or purification.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, or organic sulphonic, 2-hydroxyethane sulphonic, toluene-p-sulphonic, or naphthalene-2-sulphonic acid.

The present invention includes esters of the formula (I) compounds, such esters being for example aliphatic esters such as alkyl esters.

The esters of the compounds of formula I may be pharmaceutically acceptable metabolically labile esters of compounds of formula I. These are ester derivatives of compounds of formula I that are hydrolyzed in vivo to afford said compound of formula I and a pharmaceutically acceptable alcohol. Examples of metabolically labile esters include esters formed with (1–6C) alkanols in which the alkanol moiety may be optionally substituted by a (1–8C) alkoxy group, for example methanol, ethanol, propanol and methoxyethanol. The most preferred esters are alkyl esters derived from (1–4C) alkanols, especially methyl and ethyl esters.

The invention also comprises a process for preparing a compound according to formula (I), or a salt or ester thereof, which comprises:

(a) deprotecting a compound of formula

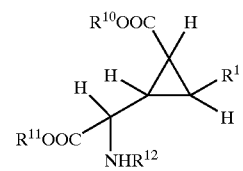

II in which $R^{10}$ and $R^{11}$ each independently represents hydrogen or a carboxyl protecting group, and $R^{12}$ represents hydrogen or an amine protecting group;

(b) hydrolysing a compound of formula

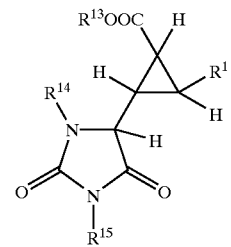

III in which $R^{13}$ represents a hydrogen atom or a carboxyl protecting group, and $R^{14}$ and $R^{15}$ each independently represents a hydrogen atom, a $C_{1-4}$ alkyl group, or a phenyl $C_{1-4}$ alkyl group in which the phenyl group is unsubstituted or substituted by halo, $C_{1-4}$ alkyl, $C_{1-4}$ alkoxy or $C_{3-4}$ alkenyl; or (c) hydrolysing a compound of formula

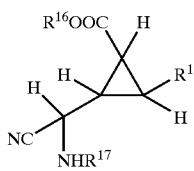

IV in which $R^{16}$ represents a hydrogen atom or a carboxy protecting group, and $R^{17}$ represents a hydrogen atom or an amine protecting group;
followed when necessary by recovering a diastereomer or isomer of the compound, or
forming a salt or ester thereof.

The protection of carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl ($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula $R^{18}CO$ in which $R^{18}$ represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy. Preferred amino protecting groups include t-butoxycarbonyl (Boc) and benzyl.

Examples of particular values for $R^{10}$, $R^{11}$, $R^{13}$ and $R^{16}$ are hydrogen, methyl, ethyl, n-propyl, n-butyl, t-butyl, benzyl, 4-methoxybenzyl, phenylethyl and phenylpropyl.

Examples of particular values for $R^{12}$ and $R^{17}$ include acetyl and tert-butoxycarbonyl.

Examples of particular values for $R^{14}$ and $R^{15}$ are hydrogen and benzyl.

The compounds of formula (II) may be deprotected by conventional methods. Thus, an alkyl carboxyl protecting group may be removed by hydrolysis. The hydrolysis may conveniently be performed by heating the compound of formula (II) in the presence of either a base, for example an alkali metal hydroxide such as lithium, sodium or potassium hydroxide, or an alkaline metal hydroxide, such as barium hydroxide or an acid such as hydrochloric acid. The hydrolysis is conveniently performed at a temperature in the range of from 20° C. to 300° C. An aralkyl carboxyl protecting group may conveniently be removed by hydrogenation. The hydrogenation may be effected by reacting the compound of formula (II) with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° C. to 100° C.

An acyl, amine protecting group is also conveniently removed by hydrolysis, for example as described for the removal of an alkyl carboxyl protecting group. Thus, a tert-butoxycarbonyl, amine protecting group may conveniently be removed in the presence of an acid, for example hydrochloric acid or trifluoroacetic acid. The hydrolysis is performed in the presence of a solvent such as water, ethyl acetate or dichloromethane and at a temperature in the range of from 20° C. to 100° C.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50° C. to 150° C.

The compounds of formula IV are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water, or in an alkanol such as methanol or ethanol, and at a temperature in the range of from 20° C. to 200° C.

Compounds of formula I in the form of diastereomeric mixtures or isomers may be obtained in a conventional manner, for example by chiral synthesis using chiral starting materials, or by using conventional separation techniques, for example by forming a crystalline salt with a chiral acid or base, or by chiral hplc.

Compounds of formula (II) in which $R^{11}$ represents hydrogen may be prepared by a procedure analogous to that described in Ohfune Y., et al., J. Med. Chem., 1996, 39, 407–423. Thus they may be prepared by reacting a compound of formula

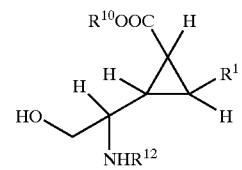

V with an oxidising agent. Convenient oxidising agents include Jones Reagent.

Compounds of formula (V) may be prepared by reacting a compound of formula

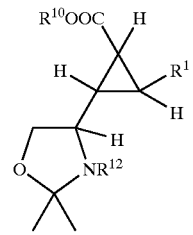

VI with a sulfonic acid, such as camphorsulfonic acid (CSA) and an alkanol, such as methanol.

Compounds of formula (VI) may be prepared by reacting a compound of formula

VII

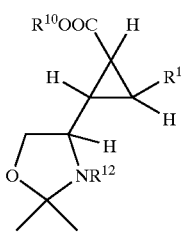

with a strong base, such as potassium bis(trimethylsilyl) amide.

Compounds of formula (VII) may be prepared by reacting a compound of formula

VIII

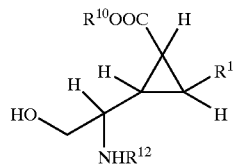

with acetone dimethyl ketal in the presence of a sulfonic acid, such as camphorsulfonic acid.

Compounds of formula VIII may be prepared by selectively deprotecting a compound of formula

IX

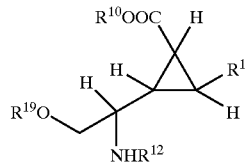

in which $R^{19}$ represents a hydroxyl protecting group, such as a tert-butyldimethylsilyl (TBS) group. A convenient reagent for removing a TBS group is camphorsulfonic acid in methanol.

The compounds of formula (IX) may be prepared by reacting a compound of formula

X

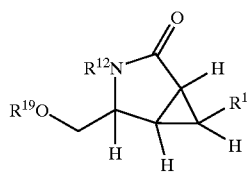

with a base, such as lithium hydroxide, for example in tetrahydrofuran, followed by introduction of the protecting group $R^{10}$, for example by treatment with diazomethane (to afford a compound in which $R^{10}$ is methyl).

Compounds of formula (X) may be prepared by treating a compound of formula

XI

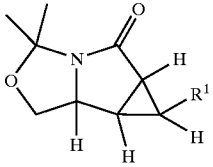

with an ion exchange resin, such as DOWEX 50Wx8, followed by introduction of the protecting groups $R^{12}$ and $R^{19}$, for example by stepwise reaction with tributylsilyl chloride in the presence of imidazole, followed by $Boc_2O$ in the presence of triethylamine and 4-dimethylaminopyridine.

Compounds of formula (XI) may be prepared by reacting a compound of formula

XII

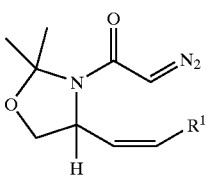

with palladium (II) acetate.

Compounds of formula (XII) may be prepared by diazotizing a compound of formula

XIII

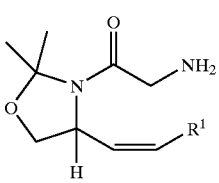

for example by reaction with sodium nitrite.

Compounds of formula (XIII) may be prepared by selectively deprotecting a compound of formula

XIV

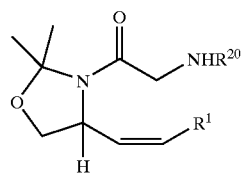

in which $R^{20}$ represents an amine protecting group, such as t-butoxycarbonyl. For example a t-butoxycarbonyl (Boc) group may conveniently be removed by treatment with trimethylsilyl trifluoromethanesulfonate (TMSOTf) and 2,6-lutidine.

The compounds of formula (XIV) may be prepared by reacting a compound of formula

XV

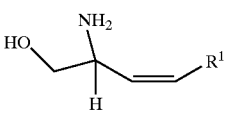

with an N-protected glycinate, such as N-hydroxysuccinimide N-(tert-butoxycarbonyl)glycinate, followed by reaction with acetone dimethylketal in the presence of a sulfonic acid such as p-toluenesulfonic acid.

The compounds of formula (XV) may be prepared by reacting a compound of formula

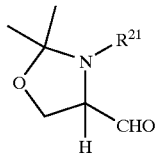

XVI in which $R^{21}$ represents an amine protecting group, such as t-butoxycarbonyl, with a triphenylphosphine halide of formula $Ph_3P^+CH_2R^1$ $A^-$, in which $A^-$ represents a halide ion such as bromide, in the presence of a strong base, such as potassium bis(trimethylsilyl)amide, followed by removal of the amine protecting group, and hydrolysis of the acetonide, for example by reaction with methanolic HCl.

Compounds of formula (II) in which $R^1$ represents $(CH_2)_nY$ in which n is 1 or 2 may alternatively be prepared by reacting a compound of formula

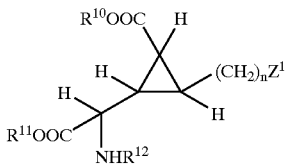

XVII in which n is 1 or 2 and $Z^1$ represents a leaving atom or group, such as a halogen atom, for example a chlorine atom, an organosulfonyloxy group, for example a p-toluenesulfonyloxy group or a diphenylphosphoryloxy group, with a salt of formula MY in which M represents an alkali metal such as sodium or potassium.

The compounds of formula (XVII) in which $Z^1$ represents a halogen atom or an organosulfonyloxy group may be prepared by reacting a compound of formula

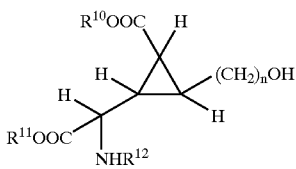

XVIII with a halogenating or sulphonating reagent such as p-toluenesulfonyl chloride.

Compounds of formula (XVII) in which $Z^1$ represents a diphenylphosphoryloxy group may be prepared by reacting a compound of formula (XVIII) with diphenyl-phosphoryl azide in the presence of diazabicyclo[5.4.0]-undec-7-ene. Convenient solvents include aromatic hydrocarbons, such as toluene. The reaction is conveniently effected at a temperature of from 0 to 100° C.

Compounds of formula (XVIII) may be converted directly into compounds of formula (II) in which $R^1$ represents $(CH_2)_nY$ and Y is $N_3$ by reaction with diethylazodicarboxylate and triphenylphosphine followed by diphenylphosphoryl azide. The reaction is conveniently conducted in an anhydrous ether solvent, such as tetrahydrofuran and under an inert atmosphere, such as nitrogen. The temperature is conveniently in the range of from −50 to 40° C.

Compounds of formula (XVII) in which $Z^1$ represents a diphenylphosphoryloxy group, may be also converted into compounds of formula (II) in which $R^1$ represents $(CH_2)_nY$ and Y is $N_3$ by reaction with sodium azide. The reaction is conveniently conducted in an anhydrous solvent, such as N,N-dimethylformamide and under an inert atmosphere, such as nitrogen. The temperature is conveniently in the range of from 0 to 100° C.

Compounds of formula (XVIII) may be converted directly into compounds of formula (II) in which $R^1$ represents $(CH_2)_nY$ and Y is F by reaction with a fluorinating agent, such as (diethylamino)sulfur trifluoride. Convenient solvents for the reaction include halogenated hydrocarbons, such as dichloromethane. The reaction is conveniently performed at a temperature of from 0 to 100 ° C.

Compounds of formula (XVIII) may be converted directly into compounds of formula (II) in which $R^1$ represents $(CH_2)_nY$ and Y is Cl by reaction with a chlorinating agent, such as carbon tetrachloride and triphenylphosphine. Convenient solvents for the reaction include amides, such as dimethylformamide. The reaction is conveniently performed at a temperature of from 0 to 100° C.

Compounds of formula (XVIII) may be converted directly into compounds of formula (II) in which $R^1$ represents $(CH_2)_nY$ and Y is $S(O)_pR^4$ and p is 0 by reaction with a compound of formula $R^4SH$, diethylazodicarboxylate and triphenylphosphine. The reaction is conveniently conducted in an anhydrous ether solvent, such as tetrahydrofuran and under an inert atmosphere, such as argon. The temperature is conveniently in the range of from −10 to 100° C. If, instead of a compound of formula $R^4SH$, thioacetic acid is used, the resultant compound is a compound of formula (II) in which Y is $SCOCH_3$ and this, on deprotection according to process step (a) above, affords a compound of formula (I) in which Y is SH. Alternatively the compound of formula (XVIII) may be reacted with a disulfide of formula $(R^4S)_2$ and tributylphosphine. The reaction is conveniently conducted in an anhydrous ether solvent, such as tetrahydrofuran and under an inert atmosphere, such as argon. The temperature is conveniently in the range of from −10 to 100° C. Compounds of formula (II) in which $R^1$ represents $(CH_2)_nY$, Y is $S(O)_pR^4$ and p is 0 may be converted into the corresponding compounds in which p is 1 or 2 by reaction with a peracid, such as m-chloroperbenzoic acid. Convenient solvents include halogenated hydrocarbons, such as dichloromethane. The reaction is conveniently performed at temperature in the range of from −10 to 50° C.

Compounds of formula (XVIII) may be converted directly into compounds of formula (II) in which $R^1$ represents $(CH_2)_nY$ and Y is 5-phenyltetrazol-2-yl by reaction with 5-phenyl-1H-tetrazole, diethyl azodicarboxylate and triphenylphosphine. The reaction is conveniently conducted in an anhydrous ether solvent, such as tetrahydrofuran and under an inert atmosphere, such as nitrogen. The temperature is conveniently in the range of from 0 to 100° C.

The compounds of formula XVIII may be prepared either by hydrolysing a compound of formula XIX

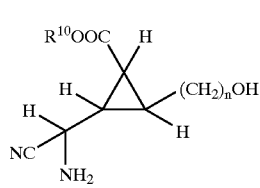

XIX for example using HCl in aqueous ethanol, followed by protecting the amino group, for example by reaction with Boc$_2$O in tetrahydrofuran or dioxane in the presence of NaHCO$_3$, or by hydrolysing a compound of formula XX

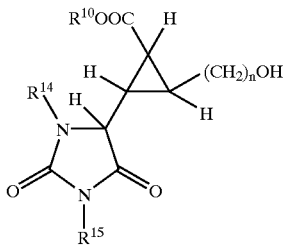

XX in the presence of a base, for example sodium hydroxide, in an aqueous solution at an elevated temperature, for example about 100° C., followed by protecting the carboxylic acid groups, for example using HCl in anhydrous ethanol, and protecting the amino group, for example by reaction with Boc$_2$O in tetrahydrofuran or dioxane in the presence of NaHCO$_3$.

The compounds of formula XIX may be prepared by reacting a compound of formula XXI

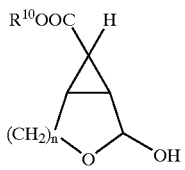

XXI with ammonium chloride and potassium cyanide in the presence of aluminium oxide. A convenient solvent is acetonitrile.

The compounds of formula XX may be prepared by hydrolysing a compound of formula XXI with an alkali metal hydroxide, for example using sodium hydroxide in aqueous ethanol, followed by treatment with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C.

Compounds of formula XXI in which n is 1 may be prepared by oxidising a compound of formula XXII

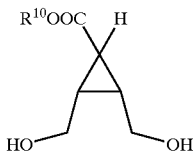

XXII for example by employing a Swern oxidation.

Compounds of formula XXII may be prepared by reacting a compound of formula

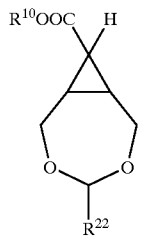

XXIII in which R$^{22}$ represents a hydrogen atom, a C$_{1-4}$ alkyl group or a phenyl group, with HCl or camphorsulphonic acid in an alkanol such as ethanol.

Compounds of formula XXIII may be prepared by reacting a compound of formula

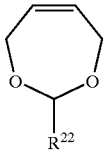

with N$_2$CHCO$_2$R$^{10}$ in the presence of Rh$_2$(OAc)$_4$. A convenient solvent is pentane.

Compounds of formula XXI in which n is 2 may be prepared by reducing a compound of formula (XXIg)

for example using diisobutylaluminium hydride.

Compounds of formula (XXIg) may be prepared by reacting a compound of formula (XXIh)

with a peracid, such as m-chloroperbenzoic acid.

After they have been prepared, compounds of formula (II) may be converted into other compounds of formula (II) prior to deprotection according to process step (a) hereinabove. For example, a compound of formula (II) in which R$^1$ is (CH$_2$)$_n$Y and Y is N$_3$ may be reduced in the presence of an alkylating, such as a C$_{1-4}$ alkyl or aryl-C$_{1-4}$ alkyl halide to afford a compound of formula (II) in which R$^1$ is (CH$_2$)$_n$Y, Y is NHR$^5$, and R$^5$ is C$_{1-4}$ alkyl or aryl-C$_{1-4}$ alkyl. The reduction is conveniently performed by catalytic hydrogenation in the presence of a Group VIII metal catalyst, such as palladium on carbon or platinum oxide. Similarly, a compound of formula (II) in which R$^1$ is (CH$_2$)$_n$Y and Y is NHCOR$^8$ may be prepared by reducing a compound of formula (II) in which R$^1$ is (CH$_2$)$_n$Y and Y is N$_3$ in the presence of an anhydride of formula (R$^8$CO)$_2$CO. The reduction is conveniently performed by catalytic hydrogenation in the presence of a Group VIII metal catalyst, such as palladium on carbon or platinum oxide. Alternatively, the reduction and alkylation or acylation steps may be performed sequentially. It will be appreciated by those skilled in the art that deprotection of a compound of formula (II) in which $R^1$ is $(CH_2)_nY$ and Y is $NHCOR^8$ according to process step (a) may, depending upon the reaction conditions selected, afford a compound of formula (I) in which Y is $NHCOR^8$ or $NH_2$.

A compound of formula (II) in which $R^1$ is $(CH_2)_nY$ and Y is CN may be converted directly into a compound of formula (I) in which $R^1$ is $(CH_2)_nY$ and Y is COOH by acid catalysed hydrolysis, for example using hydrochloric acid.

A compound of formula (II) in which $R^1$ is $(CH_2)_nY$ and Y is CN may be converted into a compound of formula (II) in which $R^1$ is $(CH_2)_nY$ and Y is 1H-tetrazol-5-yl by reaction with a trialkyltin azide such as tributyltin azide.

A compound of formula (II) in which $R^1$ is $(CH_2)_nY$ and Y is $NH_2$ may be converted into a compound of formula (II) in which $R^1$ is $(CH_2)_nY$ and Y is $NO_2$ by reaction with a peracid, such as m-chloroperbenzoic acid.

The compounds of formula (III) may be prepared by reacting a compound of formula

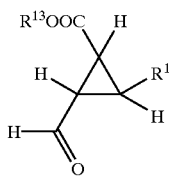

XXV with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C. If desired, the compounds of formula (III) may then be alkylated, for example using a compound of formula $R^{14}Cl$ or $R^{15}Cl$. The alkylated compounds are readily separated into their diastereomers.

Compounds of formula (IV) may be prepared by reacting a compound of formula (XXV), in which $R^{16}$ is as defined for $R^{13}$, with an alkali metal cyanide, such as lithium, sodium or potassium cyanide, and an ammonium halide, such as ammonium chloride. It has been found advantageous to perform the reaction in the presence of ultrasound. Thus, the ammonium halide and alkali metal cyanide are advantageously mixed with chromatography grade alumina in the presence of a suitable diluent, such as acetonitrile. The mixture is then irradiated with ultrasound, whereafter the compound of formula XXV is added, and the mixture is again irradiated.

The resultant mixture of diastereoisomeric aminonitriles may then be reacted with an acylating agent, such as acetyl chloride in the presence of a suitable base, for example an amine such as diisopropylamine, and in the presence of a suitable solvent such as dichloromethane, to afford a mixture of diastereomeric acylaminonitriles. The desired stereoisomer may conveniently be separated from this mixture, for example by chromatography.

The compounds of formula (XXV) may be prepared by oxidising a compound of formula

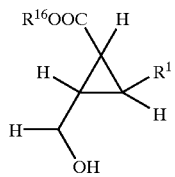

XXVI for example by a Swern oxidation or by reaction with tetrapropylammonium perruthenate and N-methylmorpholine-N-oxide in the presence of a molecular sieve (4 Å).

A compound of formula (XXV) having the configuration

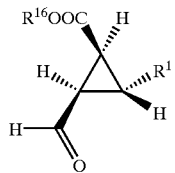

may be converted into a mixture of compounds of formula (XXV) containing a compound of the configuration

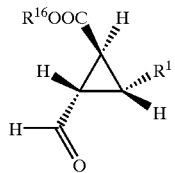

by treatment with methanolic sodium hydroxide, if necessary followed by reintroduction of the protecting group $R^{16}$, for example by reaction with diazomethane to afford a compound in which $R^{16}$ is methyl.

The compounds of formula (XXVI) may be prepared by selectively deprotecting a compound of formula

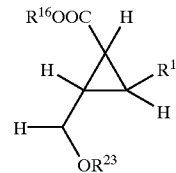

XXVII in which $R^{23}$ represent a hydroxyl protecting group, for example a benzyl group. The deprotection may be performed in a conventional manner. For example, a benzyl group may be removed by catalytic hydrogenation using palladium on charcoal as catalyst.

Compounds of formula (XXVI) having the configuration

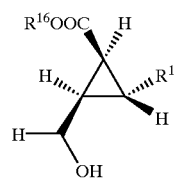

may be prepared by reacting a compound of formula

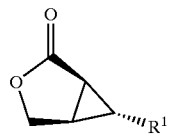

XXVIII with an alkali metal hydroxide, such as lithium hydroxide, to afford a compound in which $R^{16}$ represents hydrogen, followed by followed by introducing a protecting group $R^{16}$, for example by reaction with diazomethane to produce a compound in which R is methyl.

The compounds of formula (XXVIII) may be prepared by reacting a compound of formula

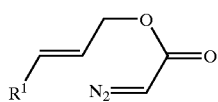

XXIX with Cu(TBS)$_2$.(copper (II) N-(tert-butyl)salicylaldimine).

The compounds of formula (XXIX) may be prepared by reacting a compound of formula

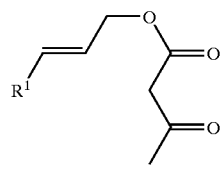

XXX with a sulfonyl azide such as p-acetamidobenzenesulfonyl azide in the presence of a base, such as triethylamine, followed by reaction with an aqueous alkali metal hydroxide, such as lithium hydroxide.

The compounds of formula (XXX) may be prepared by reacting a compound of formula

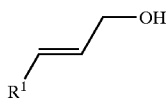

XXXI with diketene in the presence of an alkali metal acetate, such as sodium acetate.

Compounds of formula (XXV) in which $R^1$ represents fluoromethyl may be prepared by protecting one hydroxy group in a diol compound of formula (XXII), for example with a benzyl group, followed either by reaction with a fluorinating agent, such as (diethylamino)sulfur trifluoride, or by functionalization of the remaining hydroxyl group with a leaving atom or group such as an iodine atom or p-toluenesulfonyloxy group then reaction with an alkali metal fluoride), followed by removal of the hydroxy protecting group.

Compounds of formula (II) may also be prepared by reacting a compound of formula

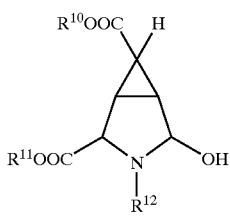

XXXII with a Wittig reagent. For example, a compound of formula (XXXII) may be reacted with a haloalkyl triphenylphosphonium bromide to afford a compound of formula (II) in which $R^1$ represents a haloalkenyl group. The resultant product may then, if desired, be converted into another compound of formula (II), for example by catalytic hydrogenation to convert a haloalkenyl group to a haloalkyl group.

Compounds of formula (XXXII) may be prepared by Swern oxidation of a compound of formula (II) in which $R^1$ represents hydroxymethyl.

It will be appreciated that in order to obtain a compound of formula I which is in the configuration of formula Ia, the intermediates must be prepared in the appropriate configurations. The following formula illustrate the respective configurations for each of the intermediates.

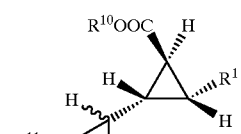

IIa

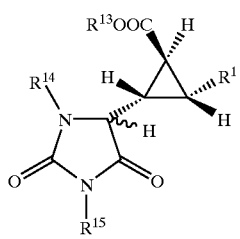

IIIa

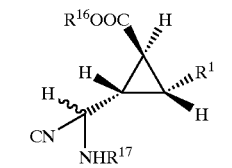

IVa

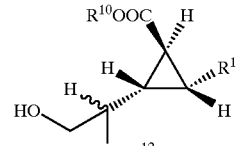

Va

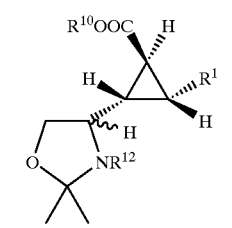

VIa

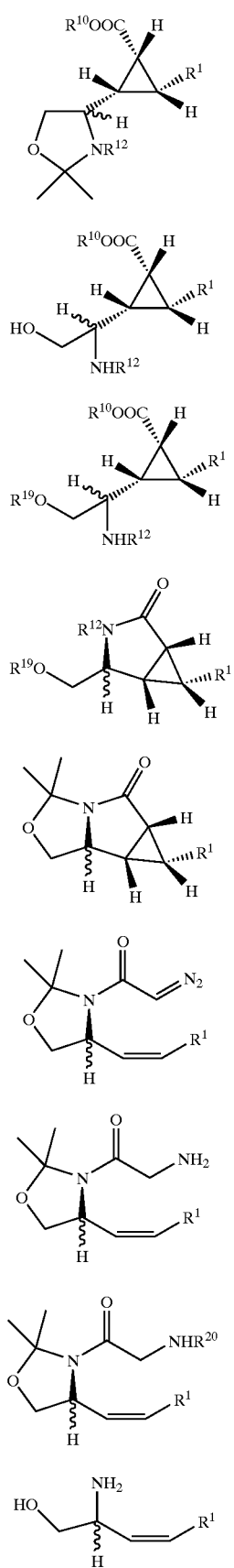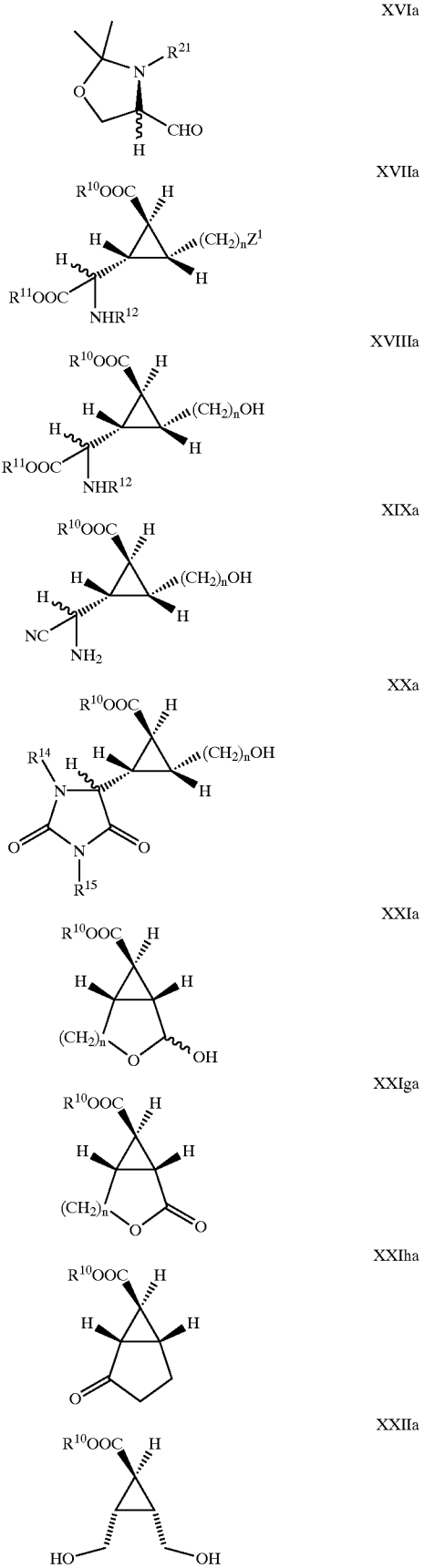

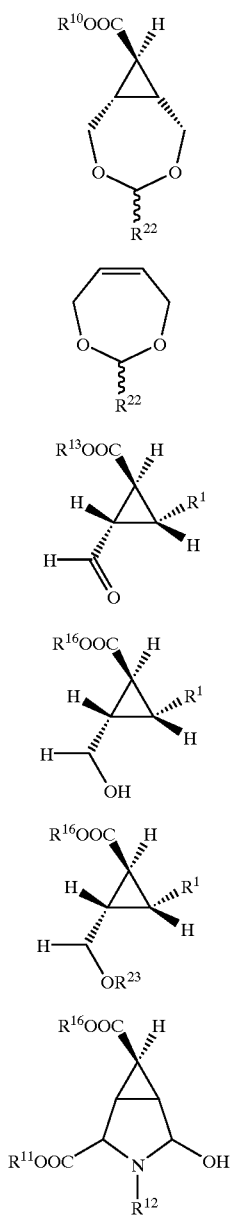

As described hereinabove, the compounds of the invention are useful for the treatment of disorders of the central nervous system.

According to another aspect therefore, the present invention provides a method of treating a patient suffering from or susceptible to a disorder of the central nervous system, which comprises administering an effective amount of a compound of formula I as defined hereinabove, or a pharmaceutically acceptable metabolically labile ester thereof, or a pharmaceutically acceptable salt thereof.

The particular effective amount or dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in patients associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester thereof, or a pharmaceutically acceptable salt thereof.

The formula I compounds of the present invention are also believed to have the ability to treat a variety of other neurological disorders in patients that are associated with glutamate dysfunction, including muscular spasms, convulsions, migraine headaches, urinary incontinence, psychosis, (such as schizophrenia), drug tolerance and withdrawal (such as nicotine, opiates and benzodiazepines), anxiety and related disorders, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester thereof, or a pharmaceutically acceptable salt thereof.

The term "treating" for purposes of the present invention, includes prophylaxis, amelioration or elimination of a named condition once the condition has been established.

The term "patient" for purposes of the present invention is defined as any warm blooded animal such as, but not limited to, a mouse, guinea pig, dog, horse, or human. Preferably, the patient is human.

According to another aspect, the present invention provides a compound of formula I as defined hereinabove, or a pharmaceutically acceptable metabolically labile ester thereof, or a pharmaceutically acceptable salt thereof, for use as a pharmaceutical.

According to yet another aspect, the present invention provides the use of a compound of formula I as defined hereinabove, or a pharmaceutically acceptable metabolically labile ester thereof, or a pharmaceutically acceptable salt thereof, for the manufacture of a medicament for treating a disorder of the central nervous system.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., *Neuropharmacol.,* 1996, 35, 1661–1672 and 1997, 36, 1–11).

In these tests the compound of Example 1 of the present application was found to reverse [3H] LY341495 binding with a Ki of 66.1 nM at mGluR2 and 7.9 nM at mGluR3 (average result from several tests). The compound of Example 22, which is an anantiomer of the compound of Example 1, was found to give a Ki of 30.5 nM for mGluR2 and 5.1 nM for mGluR3. (LY341495 is described in Ornstein et al., J. Med. Chem., 1998, 41, 346–357 and J. Med. Chem., 1998, 41, 358 to 378).

The ability of compounds to function as agonists of glutamate at metabotropic glutamate receptors may be determined by measuring their ability to decrease forskolin-stimulated cAMP in cells expressing mGluR receptors. The compound of Example 1 gave an $EC_{50}$ in this test of 5.2 nM for mGluR2 and 11.5 nM for mGluR3.

The ability of compounds of formula I to treat anxiety and related disorders may be demonstrated using the well known fear-potentiated startle and elevated plus maze models of anxiety, as described in Davis, Psychopharmacology, 62:1; 1979, Lister, Psychopharmacology, 92: 180–185; 1987 and U.S. Pat. No. 5,750,566. The compound of Example 1 has been found to be highly potent in an animal model of anxiety.

The compounds of the present invention are preferably formulated prior to administration. Therefore, another aspect of the present invention is a pharmaceutical formulation comprising a compound of formula I, a pharmaceutically acceptable metabolically labile ester thereof, or a pharmaceutically acceptable salt thereof, and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard Gelatin Capsules are Prepared Using the Following Ingredients

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets Each Containing 60 mg of Active Ingredient are Made as Follows

| Active Ingredient | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The following Examples illustrate the invention. In the Examples, the term "Garner's aldehyde" signifies 1,1-dimethylethyl (S) or (R)-4-formyl-2,2-dimethyl-3-oxazolidine carboxylate, $Ph_3PEtBr$ signifies (ethyl) triphenylphosphonium bromide, KHMDS and LiHMDS signify potassium and lithium bis(trimethylsilyl)amide respectively, $Et_2O$ signifies diethylether, AcOEt signifies ethyl acetate, MeOH signifies methanol, Boc signifies t-butoxycarbonyl, $Et_3N$ signifies triethylamine, THF signifies tetrahydrofuran, TMSOTf signifies trimethylsilyl trifluoromethanesulfonate, $Pd(OAc)_2$ signifies palladium acetate, DMF signifies dimethylformamide, DMAP signifies 4-dimethylaminopyridine, Jones Reagent signifies a solution of 1.0 g of $Na_2Cr_2O_7.2H_2O$ and 1.34 g of sulfuric acid in $H_2O$ (total volume 5 ml), DBU signifies 1,8-diazabicyclo [5.4.0]undec-7-ene and DME signifies ethylene glycol dimethyl ether.

Example 1

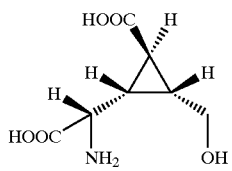

(2SR, 1'SR, 2'RS, 3'RS)-2-(3'-hydroxymethyl-2'-carboxycyclopropyl) glycine a) Ethyl 2,3-dihydroxymethylcyclopropane carboxylate

To a solution of cis-4,7-dihydro-1,3-dioxepin (4.57 g, 45.6 mmol) in pentane (25 mL) under nitrogen at room temperature, $Rh_2(OAc)_4$ (220 mg, 0.5 mmol) was added. To the resulting suspension vigorously stirred, a solution of ethyl diazoacetate (10.5 mL, 100 mmol) in pentane (75 mL) was added dropwise at room temperature over a period of 3–4 hours. After the addition was completed, solvent was removed under vacuo and residue was chromatographed using a gradient of AcOEt/Hexane 1:10 to 1:5 as eluent. 6.75 g of an inseparable mixture of cyclopropanated product and $EtO_2CCH=CHCO_2Et$ was obtained. A solution of this mixture in ethanol saturated with hydrogen chloride (250 mL) was stirred overnight at room temperature. The following day, solvent was removed under vacuo and residue taken into ethanol (100 mL). This solution was neutralized with $NaHCO_3$ (solid), filtered and concentrated. The resulting residue was chromatographed using a gradient of AcOEt/Hexane 1:1 to 3:1 as eluent to give 4.3 g (56% yield) of diol. $^1$H-NMR (200 MHz, $CDCl_3$): 1.23 (t, J=7.1 Hz, 3H), 1.49 (t, J=3.5, 1H), 1.89–2.00 (m, 2H), 2.72 (br s, 2H), 3.31–3.42 (m, 2H), 4.05–4.16 (m, 2H) and 4.10 ppm (c, J=7.1 Hz, 2H).

$^{13}$NMR (50 MHz, $CDCl_3$): 14.0, 23.8, 27.1 (2C), 60.3 (2C), 60.8 and 172.8 ppm.

b) (2SR) and (2RS) Ethyl (1RS,5SR,6RS)-2-hydroxy-3-oxabicyclo [3.1.0]-hexane-6-carboxylate To a solution of oxalyl chloride (0.38 mL, 4.48 mmol) in $CH_2Cl_2$ (20 mL) at −78° C. under nitrogen atmosphere, dimethylsulfoxide (0.66 mL, 9.33 mmol) was added and stirred for 20 minutes. To this mixture, a solution of the product of step a) (650 mg, 3.73 mL) in $CH_2Cl_2$ was added and reaction was stirred at the same temperature for 30 minutes. Then, triethylamine (2.6 mL, 18.65 mmol) was added and mixture allowed to react at room temperature. After 30 minutes, the reaction mixture was quenched with water, the layers were separated and the aqueous layer was extracted with $CH_2Cl_2$ (2×). The combined organic layers were dried ($Na_2SO_4$), filtered and evaporated to give a residue which was chromatographed using a gradient of AcOEt/Hexane 1:2 to 1:1 as eluent to give 470 mg (73% yield) of lactol. $^1$H-NMR (200 MHz, $CDCl_3$): 1.23 (t, J=7.1 Hz, 3H), 1.43 (t, J=3.3 Hz, 1H), 2.21–2.23 (m, 2H), 2.76 (d, J=3.0 Hz, 1H), 3.85 (d, J=8.7 Hz, 1H), 4.06 (d, J=8.7 Hz, 1H), 4.10 (c, J=7.1 Hz, 2H) and 5.32 (d, J=3.0 Hz, 1H). $^{13}$C-NMR (50 MHz, $CDCl_3$): 14.1, 22.1, 25.0, 31.2, 60.8, 67.3, 97.8 and 171.9 ppm.

c) (2SR) and (2RS)-2-(1'SR,2'RS,3'RS)-2'-(ethoxycarbonyl)-3'-hydroxymethylcyclopropyl] glycinonitrile A suspension of ammonium chloride (2.42 g, 45.3 mmol) and neutral aluminium oxide (1.4 g) in acetonitrile (50 mL) was ultrasonicated for one hour. A solution of the product of step b) (780 mg, 4.53 mmol) in acetonitrile (20 mL) was then added and ultrasonicated for one hour. After potassium cyanide (3.54 g, 54.36 mmol) finely powdered was added, the mixture was allowed to react for 15 hours. Then, additional aluminium oxide (3.2 g) was added and the reaction mixture was ultrasonicated for 4 days. The mixture was then filtered through celite and the inorganics washed with acetonitrile to give 710 mg (78% yield) of the four possible aminonitriles as a yellow oil.

d) (Alternative 1) Ethyl (2SR,1'SR,2'RS,3'RS)-N-(tert-butoxycarbonyl)-2-[2'-(ethoxycarbonyl)-3'-hydroxymethylcyclopropyl]glycinate A solution of the product of step c) (380 mg, 1.92 mmol) in ethanol saturated with hydrogen chloride (20 mL) and $H_2O$ (0.10 mL, 5.75 mmol) was stirred for one hour at 0° C. and for 48 hours at room temperature. The following day, the solvent was removed in vacuo and the residue was dissolved in ethanol (25 mL). Then, the solution was neutralized with $NaHCO_3$ (solid), filtered through celite and concentrated to dryness. The resulting residue was taken into dioxane(20 mL), and a saturated aqueous solution of $NaHCO_3$ (5 mL) was added. Then, a solution of di-tert-butyldicarbonate (500 mg, 2.3 mmol) in dioxane (5 mL) was added and mixture stirred overnight. The layers were then separated and the aqueous layer was extracted with ethyl acetate (AcOEt). The combined organic layers were dried ($Na_2SO_4$), filtered and concentrated to dryness. The residue was purified by column chromatography using AcOEt/Hexane 1:2 as eluent to give 400 mg of a 1:2 mixture of diastereoisomers (61% overall yield). The minor and desired isomer (lower Rf) was separated by column chromatography using AcOEt/Hexane 1:3 as eluent giving rise to ethyl (2SR,1'SR,2'RS,3'RS)-N-(tert-butoxycarbonyl)-2-[2'-(ethoxycarbonyl)-3'-hydroxymethylcyclopropyl]glycinate as a mixture of enantiomers.

d) (Alternative 2) Ethyl (2SR,1'SR,2'RS,3'RS)-N-(tert-butoxycarbonyl)-2-[2'-(ethoxycarbonyl)-3'-hydroxymethylcyclopropyl]glycinate A solution of the product of step b) (1.8 g, 10.45 mmol) in EtOH (65 mL) and NaOH(1N) (63 mL, 63.0 mmol) was stirred at 60° C. for 1 hour. The mixture was then cooled to 0° C and the pH was adjusted to ~6 by addition of 1N $KHSO_4$. To the resulting solution, $(NH_4)_2CO_3$ (10.1 g, 104.5 mmol) and NaCN (1.02 g, 20.9 mmol) were added. The mixture was stirred under reflux overnight (16–17 hours) and then cooled to room temperature. The solution was then evaporated to dryness under vacuo to give a residue that was taken into MeOH and filtered off. The inorganics were washed with MeOH and the combined methanolic filtrates were concentrated in vacuo. The resulting residue was dissolved in 1N NaOH (200 mL) and the mixture was stirred under reflux for 48 hours and then cooled to 0° C. The pH was then adjusted to 1–2 by addition of 1N HCl, and the solvent was removed under vacuo.

The resulting residue was dissolved in a 1N HCl/ethanol solution (250 mL) and the mixture was stirred overnight at room temperature. The solvent was then removed under vacuo and the residue was taken into EtOH (200 mL). After the solvent was removed under vacuo, the residue was again taken into EtOH (200 mL) and the solution neutralized with $NaHCO_3$ (solid), the inorganics filtered off and the filtrate concentrated to dryness. The residue was taken into dioxane (200 mL) at room temperature and a saturated aqueous solution of NaHCO$_3$ (50 mL) was added. Then, a solution of di-tert-butyldicarbonate (2.75 g, 12.54 mmol) in dioxane (50 mL) was added dropwise and the mixture was vigorously stirred at room temperature overnight. The mixture was then diluted with AcOEt and the layers were separated. The aqueous layer was extracted with AcOEt (2×) and the combined organic layers were dried (Na$_2$SO$_4$), filtered and concentrated to dryness. The residue was purified by column chromatography using AcOEt/hexane (1:2) as eluent to give 2.15 g of a 2.3:1 mixture of diastereoisomers (60% overall yield). The major and desired isomer (lower Rf) was separated by column chromatography using Et$_2$O/Hexane 1:1 as eluent giving rise to ethyl (2SR,1'SR,2'RS,3'RS)-N-(tert-butoxycarbonyl)-2-[2'-(ethoxycarbonyl)-3'-hydroxymethylclopropyl]glycinate as a mixture of enantiomers.

1H-NMR (200 MHz, CDCl$_3$): 1.25 (t, J=7.1 Hz, 3H), 1.32 (t, J=7.1 Hz, 3H), 1.45 (s, 9H), 1.70–1.81 (m, 2H), 1.91–2.11 (m, 1H), 3.17 (dd, J=3.1, 10.1 Hz, 1H), 3.54–3.67 (m, 1H), 3.95–4.33 (m, 6H), and 5.20 ( br d, J=7.3 Hz, 1H).

$^{13}$C-NMR (50 MHz, CDCl$_3$): 14.0, 14.1, 22.5, 28.2 (3C), 28.9, 29.2, 52.3, 60.8, 61.0, 62.5, 80.4, 155.3, 171.8 and 172.4 ppm.

e) (2SR,1'SR,2'RS,3'RS)-2-(3'-hydroxymethyl-2'-carboxycyclopropyl)glycine

To a solution of ethyl (2SR,1'SR,2'RS,3'RS)-N-(tert-butoxycarbonyl)-2-[2'-(ethoxycarbonyl)-3'-hydroxymethylcyclopropyl]glycinate (145 mg, 0.42 mmol) in THF (3.5 mL) was added 2.5N LiOH (6.7 mL, 16.8 mmol). The mixture was vigorously stirred overnight. The organic layer was separated and discarded and the aqueous layer was washed with Et$_2$O. After the aqueous solution was adjusted to pH~1 by addition of 1N HCl at 0° C., it was extracted four times with AcOEt, and the combined organic layers were dried over Na$_2$SO$_4$ and evaporated in vacuo. A solution of the residue in 2N HCl (3.5 mL) was stirred overnight. The solvent was then removed in vacuo and the resulting solid was washed with Et$_2$O. The hydrochloride was dissolved in MeOH (3 mL) and propylene oxide (10 mL) was added. The mixture was stirred overnight and the resulting insoluble solid was filtered and washed with Et$_2$O to give the title compound (55 mg, 69%).

$^1$H-NMR (200 MHz, D$_2$O): 1.77–2.11 (m, 3H), 3.62 (d, J=11.0 Hz, 1H), 3.66 (dd, J=8.6, 12.5 Hz, 1H) and 3.90 ppm (dd, J=6.0, 12.5 Hz, 1H).

$^{13}$C-NMR (50 MHz, D$_2$O): 25.0, 27.7, 29.1, 54.8, 61.0, 173.9 and 177.9 ppm.

Example 2

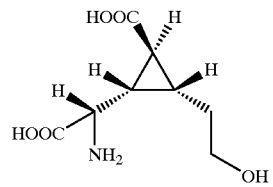

(2SR, 1'SR, 2'RS, 3'RS)-2-[(3'-(2''-hydroxyethyl)-2'-carboxy) cyclopropyl]glycine a) Ethyl (1SR,5RS,6SR)-2-oxo-bicyclo[3.1.0]hexane-6-carboxylate To a suspension of ethyl (dimethylsulfonium)acetate bromide (13.9 g, 60.9 mmol) in chloroform (60 mL), DBU (9.18 mL, 60.9 mmol) was added. The resulting suspension was vigorously stirred at room temperature for 30 minutes. Then, cyclopentenone (5.10 mL, 60.9 mmol) was added and the mixture stirred overnight at room temperature. The following day additional chloroform (60 mL) was added. The organic layer was washed with 40 mL of 0.5 N HCl, dried over magnesium sulfate, filtered and evaporated in vacuo. The residue was purified by column chromatography using ethyl acetate:hexane 1:9 as eluent to give 8.4 g (82% yield) of ethyl (1SR,5RS,6SR)-2-oxo-bicyclo[3.1.0]hexane-6-carboxylate as a colorless oil.

$^1$H-NMR (300 MHz, CDCl$_3$): 1.22 (t, J=7.1 Hz, 3H), 1.95–2.24 (m, 6H), 2.44–2.49 (m, 1H), 4.10 (q, J=7.1 Hz, 2H).

$^{13}$C-NMR (75 MHz, CDCl$_3$): 14.0, 22.3, 26.3, 29.1, 31.7, 35.6, 61.1, 170.3, 211.8 ppm.

b) Ethyl (1SR,6SR,7SR)-2-oxo-3-oxa-bicyclo [4.1.0]-heptane-7-carboxylate

To a stirred solution of ethyl (1SR,5RS,6SR)-2-oxo-bicyclo[3.1.0]hexane-6-carboxylate (34.8 g, 207.2 mmol) in dichloromethane (300 mL), 70% m-chloroperbenzoic acid (51.1 g, 207.2 mmol) was added and refluxed overnight. The following day, additional 70% m-chloroperbenzoic acid (51.1 g, 207.2 mmol) was added and reflux continued for 15 hours. After that time, the mixture was diluted with dichloromethane (200 mL), filtered and washed with 10% Na$_2$SO$_3$ (2×200 mL) and with a saturated aqueous solution of sodium bicarbonate (2×200 mL). The organic layer was dried over magnesium sulfate, filtered and evaporated in vacuo. The residue was purified by column chromatography using ethyl acetate and hexane 1:2 as eluent to give 22.89 g (60% yield) of ethyl (1SR,6SR,7SR)-2-oxo-3-oxa-bicyclo[4.1.0] heptane-7-carboxylate as a colorless oil.

$^1$H-NMR (300 MHz, CDCl$_3$): 1.24 (t, J=7.1 Hz, 3H), 1.97–2.04 (m, 1H), 2.13–2.28 (m, 3H), 2.38 (dd, J$_1$=8.3 Hz, J$_2$=3.3 Hz, 1H), 2.53 (t, J=3.9 Hz, 1H), 4.02 (td, J$_1$=8.8, Hz, J$_2$=3.3 Hz, 1H), 4.13 (q, J=7.1 Hz, 2H), 4.23–4.31 (m, 1H).

$^{13}$C-NMR (75 MHz, CDCl$_3$): 14.1, 19.4, 21.4, 22.2, 24.2, 61.5, 64.3, 167.8, 170.0 ppm.

c) (2RS) and (2SR) Ethyl (1SR,6RS,7SR)-2-hydroxy-3-oxa-bicyclo[4.1.0]heptane-7-carboxylate To a solution of ethyl (1SR,6SR,7SR)-2-oxo-3-oxa-bicyclo[4.1.0]heptane-7-carboxylate (15.2 g, 82.8 mmol) in anhydrous tetrahydrofuran (300 mL) at −78° C. and under argon, a 1.5 M solution of diisobutylaluminium hydride in toluene (82.8 mL, 124.2 mmol) in anhydrous tetrahydrofuran (150 mL) at −78° C. under an argon atmosphere was added dropwise via cannula. The solution was stirred for six hours at this temperature and then diluted with ethyl acetate (200 mL) and quenched with a saturated aqueous solution of sodium tartrate (200 mL). The resulting mixture was stirred at room temperature overnight. The organic layer was separated, dried over magnesium sulfate, filtrated and evaporated in vacuo. The residue was purified by column chromatography using ethyl acetate and hexane 1:2 as eluent to afford 12.3 g (85% yield) of (2RS) and (2SR) ethyl (1SR,6RS,7SR)-2-hydroxy-3-oxa-bicyclo[4.1.0]heptane-7-carboxylate as a colorless oil, which exist with their corresponding open hydroxyaldehyde forms.

$^1$H-NMR (300 MHz, CDCl$_3$): 1.19–1.24 (m), 1.49–1.52 (m), 1.60–1.94 (m), 2.00–2.08 (m), 2.30–2.34 (m), 2.53–2.58 (m), 3.25–3.30 (m), 3.34–3.50 (m), 3.58–3.63 (m), 3.81–3.90 (m), 4.04–4.09 (m), 5.24 ((dd, J$_1$=5.5 Hz, J$_2$=4.4 Hz), 5.29 (d, J=3.3 Hz), 9.60 (dd, J$_1$=3.3 Hz, J$_2$=1.1 Hz),.

$^{13}$C-NMR (75 MHz, CDCl$_3$): 13.9, 14.0, 14.1, 18.5, 20.6, 20.9, 21.0, 21.3, 23.7, 25.0, 25.7, 27.3, 28.6, 28.7, 34.8, 54.2, 59.9, 60.5, 60.6, 61.1, 61.6, 89.0, 90.0, 171.3, 173.3, 173.5 ppm.

d) (2SR) and (2RS)-2-(1'SR,2'SR,3'RS)-2'-(ethoxycarbonyl)-3'-(2"-hydroxyethyl)cyclopropyl] glycinonitrile A suspension of ammonium chloride (29.3 g, 547.3 mmol) and neutral aluminium oxide (54.7 g) in acetonitrile (600 mL), was ultrasonicated for one hour. To this mixture, a solution of (2RS) and (2SR) ethyl (1SR,6RS,7SR)-2-hydroxy-3-oxa-bicyclo[4.1.0]heptane-7-carboxylate (10.2 g, 54.7 mmol) in acetonitrile (200 mL) was added, and sonication was continued for an additional hour. Then, powdered potassium cyanide (42.8 g, 656.7 mmol) was added and reaction mixture was ultrasonicated for seven days. After that time, the mixture was filtered through celite and the inorganics washed with acetonitrile. The solvent was evaporated under reduced pressure to give a residue which contained a 1:1 racemic mixture of the two possible diastereomers. Both racemic aminonitriles were purified and separated by column chromatography using Acetone/Hexane 1:2 as eluent to give 3.89 g of (2SR,1'SR,2'SR,3'SR)-2'-(ethoxycarbonyl)-3'-(2"-hydroxyethyl) cyclopropyl]glycinonitrile and 3.67 g of (2RS,1'SR,2'SR,3'RS)-2'-(ethoxycarbonyl)-3'-(2"-hydroxyethyl) cyclopropyl]glycinonitrile.

e) Ethyl (2SR,1'SR,2'SR,3'RS)-N-(tert-butoxycarbonyl)-2-[2'-(ethoxycarbonyl)-3'-(2"-hydroxyethyl)cyclopropyl]glycinate To a solution of (2SR,1'SR,2'SR,3'RS)-2-[2'-(ethoxycarbonyl)-3'-(2"-hydroxyethyl) cyclopropyl]-glycinonitrile (3.88 g, 18.3 mmol) in ethanol saturated with hydrogen chloride (200 mL) at 0° C., distilled water (0.99 mL, 54.9 mmol) was added. The reaction was stirred at room temperature for four days. Then, solvent was eliminated in vacuo and residue dissolved in absolute ethanol (100 mL), neutralized with NaHCO$_3$ (solid) and stirred for 30 minutes. The inorganics were filtered and the solvent was removed under reduced pressure to dryness. The resulting residue was taken into dioxan (150 mL), and a saturated aqueous solution of NaHCO$_3$ (50 mL) was added. To this mixture, a solution of di-tert-butyldicarbonate (4.80 mg, 22.8 mmol) in dioxan (25 mL) was added and mixture stirred overnight at room temperature. The layers were then separated and the aqueous layer was extracted with ethyl acetate (2×200 mL). The combined organic layers were dried over sodium sulfate, filtered and concentrated to dryness. The residue was purified by column chromatography using ethyl acetate/hexane 1:2 as eluent to afford 3.34 g (56% yield) of ethyl (2SR,1'SR,2'SR,3'RS)-N-(tert-butoxycarbonyl)-2-[2'-(ethoxycarbonyl)-3'-(2"-hydroxyethyl)cyclopropyl] glycinate as a yellow oil.

$^1$H-NMR (300 MHz, CDCl$_3$): 1.25 (t, J=7.1 Hz, 3H), 1.30 (t, J=7.1 Hz, 3H), 1.45 (s, 9H), 1.67–1.69 (m, 2H), 1.97–2.00 (m, 1H), 3.76–3.78 (m, 2H), 4.04 (t, J=9.3 Hz, 1H), 4.11 (q, J=7.1 Hz, 2H), 4.23 (q, J=7.1 Hz, 2H), 5.33 (d, J=8.2 Hz, 1H).

$^{13}$C-NMR (75 MHz, CDCl$_3$): 14.0, 14.1, 24.3, 24.8, 28.2, 29.6, 30.9, 52.1, 60.7, 61.7, 62.0, 80.1, 155.3, 171.4, 173.2 ppm.

f) (2SR,1'SR,2'SR,3'RS)-2-[(3'-(2"-hydroxyethyl)-2'-carboxy)cyclopropyl]glycine

To a solution of ethyl (2SR,1'SR,2'SR,3'SR)-N-(tert-butoxycarbonyl)-2-[2'-(ethoxycarbonyl)-3'-(2"-hydroxyethyl)cyclopropyl]glycinate (100 mg, 0.28 mmol) in tetrahydrofuran (3.0 mL) at room temperature, a 2.5N aqueous LiOH solution (4.5 mL, 11.2 mmol) was added. The mixture was vigorously stirred overnight. The organic layer was separated and discarded and the aqueous layer was washed with diethylether. After the aqueous solution was adjusted to pH~1 by addition of 1N HCl at 0° C., it was extracted four times with AcOEt, and the combined organic layers were dried over sodium sulfate and evaporated in vacuo. A solution of the residue in a 1N solution of HCl in ethyl acetate (2.5 mL) was stirred overnight. The solvent was then removed in vacuo and the resulting solid was washed with diethylether. The resulting hydrochloride salt of the title compound was dissolved in methanol (2.0 mL) and propylene oxide (8.0 mL) was added. The mixture was stirred overnight and the resulting insoluble solid was filtered and washed with diethylether to give the title compound (34 mg, 60%).

$^1$H-NMR (200 MHz, D$_2$O): 1.46–1.84 (m, 4H), 1.92–2.05 (m, 1H), 3.44 (d, J=10.5 Hz, 1H), 3.71 (br t, J=6.4 Hz, 2H).

$^{13}$C-NMR (50 MHz, D$_2$C): 24.8, 25.7, 26.9, 29.8, 54.0, 60.9, 173.0, 178.0 ppm.

Example 3

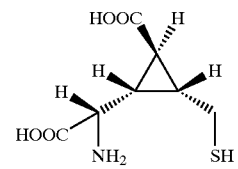

(2SR, 1'RS, 2'RS, 3'RS)-2-[3'-mercaptomethyl-2'-carboxycyclopropyl] glycine a) Ethyl (2SR,1'RS,2'RS,3'RS)-N-(tert-butoxycarbonyl)-2-[2'-(ethoxycarbonyl)-3'-(acetylthiomethyl)cyclopropyl]glycinate To a solution of triphenylphosphine (152 mg, 0.58 mmol) in dry tetrahydrofuran (1.8 mL) at 0° C. under argon, diethyl azodicarboxylate (0.091 mL, 0.58 mmol) was added dropwise. The mixture was stirred for 20 min and then a solution of thioacetic acid (0.042 mL, 0.58 mmol) and ethyl (2SR, 1'SR,2'RS,3'RS)-N-(tert-butoxycarbonyl)-2-[2'-(ethoxycarbonyl)-3'-(hydroxymethyl)cyclopropyl]glycinate (100 mg, 0.29 mmol) in dry tetrahydrofuran (0.9 mL) was added via cannula and stirred overnight at room temperature. Silicagel was added to the mixture. The solvent was removed under reduced pressure and the residue was purified by flash chromatography using hexane/ethyl acetate 4:1 as eluent to give 70 mg of ethyl (2SR,1'RS,2'RS,3'RS) N-(tert-butoxycarbonyl)-2-[2'-(ethoxycarbonyl)-3'-(acetylthiomethyl)cyclopropyl]glycinate (60% yield).

$^1$H-NMR (200 MHz, CDCl$_3$) δ: 5.02 (bs, 1H); 4.21–3.98 (dc, 6H); 3.20 (m, 1H); 3.00 (m, 1H); 2.27 (s, 3H); 1.74 (m, 1H); 1.38 (s, 9H) and 1.19 (dt, 6H) ppm.

$^{13}$C-NMR (50 MHz, CDCl$_3$) δ: 195.0; 172.2; 170.8; 155.1; 80.1; 61.8; 60.8; 51.9; 30.8; 30.4; 27.9 (3C); 27.0; 25.2; 24.9 and 14.0 (2C) ppm.

b) (2SR,1'RS,2'RS,3'RS)-2-[3'-mercaptomethyl-2'-carboxycyclopropyl]glycine.

A solution of ethyl (2SR,1'RS,2'RS,3'RS) N-(tert-butoxycarbonyl)-2-[2'-(ethoxycarbonyl)-3'-

(acetylthiomethyl)cyclopropyl]glycinate (240 mg, 0.59 mmol) in 6N HCl (5.3 mL) was heated under reflux for 16 h. The solvent was then removed in vacuo and the resulting solid was washed with diethyl ether to give the corresponding hydrochloride salt of the title compound. After purification by ion exchange chromatography, 97 mg (80% yield) of (2SR,1'RS,2'RS,3'RS)-2-[3'-mercaptomethyl-2'-carboxycyclopropyl]glycine were obtained as a white solid.

$^{13}$C-NMR (50 MHz, $D_2O$/Py-$d_5$) δ: 178.1; 171.5; 52.7; 28.4; 27.2; 26.6 and 21.7 ppm.

IR (film): 3437; 1631; 1385; 1234 and 889 cm$^{-1}$. Melting point: 200–202° C.

Example 4

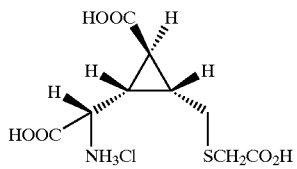

(2SR, 1'RS, 2'RS, 3'RS)-2-[3'-carboxymethylthiomethyl- 2'-carboxycyclopropyl] glycine hydrochloride a) Ethyl (2SR,1'RS,2'RS,3'RS) N-(tert-butoxycarbonyl)-2-[2'-(ethoxycarbonyl)-3'-(ethoxycarbonylmethylthiomethyl)cyclopropyl] glycinate.

To a solution of triphenylphosphine (388 mg, 1.48 mmol) in dry tetrahydrofuran (4.5 mL) at 0° C. under argon, diethyl azodicarboxylate (0.233 mL, 1.48 mmol) was added dropwise. The mixture was stirred for 20 min and then a solution of ethyl mercaptoacetate (0.133 mL, 1.48 mmol) and ethyl (2SR,1'SR,2'RS,3'RS)-N-(tert-butoxycarbonyl)-2-[2'-(ethoxycarbonyl)-3'-(hydroxymethyl)cyclopropyl]glycinate (256 mg, 0.74 mmol) in dry tetrahydrofuran (2.2 mL) was added via cannula and stirred overnight at room temperature. Silicagel was added to the mixture. The solvent was removed under reduced pressure and the residue was purified by flash chromatography using hexane/ethyl acetate 4:1 as eluent to give 143 mg of ethyl (2SR,1'RS,2'RS,3'RS) N-(tert-butoxycarbonyl)-2-[2'-(ethoxycarbonyl)-3'-(ethoxycarbonylmethylthiomethyl)cyclopropyl]glycinate (43% yield).

$^1$H-NMR (200 MHz, CDCl$_3$) δ: 4.35 (d, 1H); 4.05 (m, 6H); 3.69 (s, 2H); 3.61–3.53 (m, 3H); 2.30 (dd, 1H; J=3.0 and 7.3 Hz); 2.07 (m, 1H); 1.96 (m, 1H); 1.35–1.13 (m, 18H) ppm.

$^{13}$C-NMR (50 MHz, CDCl$_3$) δ: 171.6; 170.1; 169.6; 153.5; 80.1; 60.9; 60.6; 60.2; 52.4; 49.1; 40.9; 29.7; 28.0; 25.2; 22.6 and 13.9 ppm.

IR (film): 2976, 2934, 1743, 1728, 1709, 1456, 1381, 1273, 1190, 1124, 1041 and 958 cm$^{-1}$.

b) (2SR,1'RS,2'RS,3'RS) 2-[3'-carboxymethylthiomethyl-2'-carboxycyclopropyl] glycine hydrochloride A solution of ethyl (2SR,1'RS,2'RS,3'RS) N-(tert-butoxycarbonyl)-2-[2'-(ethoxycarbonyl)-3'-(ethoxycarbonylmethylthiomethyl)cyclopropyl]glycinate (290 mg, 0.64 mmol) in 6N HCl (6 mL) was heated under reflux for 16 h. The solvent was then removed in vacuo and the resulting solid was washed with diethyl ether to give 97 mg (52% yield) the corresponding hydrochloride salt of the title compound.

$^{13}$C-NMR (50 MHz, MeOH-$d_4$) δ: 173.3; 173.0; 169.4; 61.9; 48.5; 41.9; 28.1; 25.9 and 20.5 ppm.

IR (film): 3426; 3038; 2924; 1741; 1716; 1637; 1591; 1444; 1396; 1219 and 1182 cm$^{-1}$.

Example 5

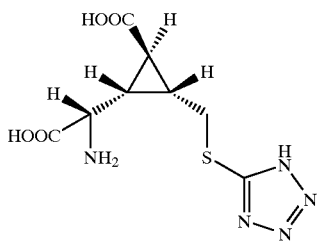

(2SR, 1'RS, 2'RS, 3'RS)-2-[3'-1H-tertrazol-5-ylthiomethyl)-2'-carboxycyclopropyl] glycine a) Ethyl (2SR,1'RS,2'RS,3'RS)-N-(tert-butoxycarbonyl)-2-[2'-(ethoxycarbonyl)-3'-(1H-tetrazol-5-ylthiomethyl)cyclopropyl]glycinate To a solution of triphenylphosphine (1.32 g, 5.03 mmol) in dry tetrahydrofuran (16 mL) at 0° C. under argon, diethyl azodicarboxylate (0.79 mL, 5.03 mmol) was added dropwise. The mixture was stirred for 20 min and then a solution of 5-mercapto-1H-tetrazole (510 g, 5.03 mmol) and ethyl (2SR,1'SR,2'RS,3'RS)-N-(tert-butoxy-carbonyl)-2-[2'-(ethoxycarbonyl)-3'-(hydroxymethyl)cyclopropyl]glycinate (870 mg, 2.52 mmol) in dry tetrahydrofuran (8 mL) was added via cannula and stirred overnight at room temperature. Silicagel was added to the mixture. Solvent was removed under reduced pressure and the residue was purified by flash chromatography using a 5% solution of acetic acid in ethyl acetate as eluent to give 430 mg of ethyl (2SR,1'RS,2'RS, 3'RS) N-(tert-butoxycarbonyl)-2-[2'-(ethoxycarbonyl)-3'-(1H-tetrazol-5-ylthiomethyl)cyclopropyl] glycinate (40% yield).

$^1$H-NMR (200 MHz, CDCl$_3$) δ: 5.30 (bs, 1H); 4.48–4.01 (m, 5H); 3.63–3.53 (dd, 1H); 3.44–3.33 (dd, 1H); 1.89–1.47 (m, 3H); 1.43 (s, 9H) and 1.33–1.16 (dt, 6H) ppm.

$^{13}$C-NMR (50 MHz, CDCl$_3$) δ: 173.0; 171.5; 156.7; 155.6; 80.2; 62.0; 61.4; 52.5; 31.7; 30.1; 28.2 (3C); 27.2; 25.6; 14.1 and 13.9 ppm.

b) (2SR,1'RS,2'RS,3'RS)-2-[3'-(1H-tetrazol-5-yl-thiomethyl)-2'-carboxycyclopropyl]glycine A solution of ethyl (2SR,1'RS,2'RS,3'RS) N-(tert-butoxycarbonyl)-2-[2'-(ethoxycarbonyl)-3'-(1H-tetrazol-5-yl-thiomethyl)cyclopropyl]glycinate (370 mg, 0.86 mmol) in 6N HCl (15 mL) was heated under reflux overnight. The solvent was then removed in vacuo and the resulting solid was washed with diethylether to give the corresponding hydrochloride salt of the title compound. After purification by ion exchange chromatography, 140 mg (60% yield) of (2SR,1'RS,2'RS,3'RS)-2-[3'-(1H-tetrazol-5-yl-thiomethyl)-2'-carboxycyclopropyl]glycine were obtained as a white solid.

$^1$H-NMR (200 MHz, $D_2O$/KOD) δ: 3.37–3.28 (dd, 1H); 3.01–2.82 (m, 2H); 1.62–1.43 (m, 2H) and 1.25 (t, 1H) ppm.

$^{13}$C-NMR (50 MHz, $D_2O$/KOD) δ: 181.6; 181.3; 158.3; 55.7; 32.8; 32.2; 29.1 and 26.0 ppm.

Example 6

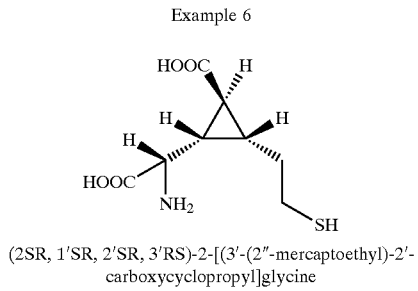

(2SR, 1'SR, 2'SR, 3'RS)-2-[(3'-(2"-mercaptoethyl)-2'-carboxycyclopropyl]glycine a) Ethyl (2SR,1'SR,2'SR,3'RS)-N-(tert-butoxycarbonyl)-2-[2'-(ethoxycarbonyl)-3'-(2"-acetylthioethyl)cyclopropyl]glycinate To a solution of triphenylphosphine (309 mg, 1.18 mmol) in dry tetrahydrofuran (3 mL) at 0° C. under argon, diethyl azodicarboxylate (0.185 mL, 1.18 mmol) was added dropwise. The mixture was stirred for 20 min and then a solution of thioacetic acid (0.091 mL, 1.18 mmol) and ethyl (2SR,1'SR,2'SR,3'RS)-N-(tert-butoxycarbonyl)-2-[2'-(ethoxycarbonyl)-3'-(2"-hydroxyethyl)cyclopropyl]glycinate (212 mg, 0.59 mmol) in dry tetrahydrofuran (6 mL) was added via cannula and stirred overnight at room temperature. Silicagel was added to the mixture. The solvent was removed under reduced pressure and the residue was purified by flash chromatography using hexane and ethyl acetate 3:1 as eluent to give 123 mg of ethyl (2SR, 1'SR, 2'SR,3'RS)-N-(tert-butoxycarbonyl)-2-[2'-(ethoxycarbonyl)-3'-(2"-acetylthioethyl)cyclopropyl]glycinate (50% yield).

$^1$H-NMR (200 MHz, CDCl$_3$) δ: 5.20 (bs, 1H); 4.26–4.04 ((m, 4H); 3.94 (bs, 1H); 3.04–2.96 (m, 2H); 2.30 (s, 3H); 1.73–1.58 (m, 5H); 1.42 (s, 9H) and 1.31–1.21 (m, 6H) ppm.

$^{13}$C-NMR (50 MHz, CDCl$_3$) δ: 195.2; 172.8; 171.1; 155.2; 80.1; 61.6; 60.6; 52.1; 30.8; 30.5; 29.8; 29.3; 28.1 (3C); 26.7; 25.6; 14.1 and 14.0 ppm.

b) (2SR,1'SR,2'SR,3'RS) 2-[3'-(2"-mercaptoethyl)-2'-carboxycyclopropyl]glycine A solution of ethyl (2SR,1'SR,2'SR,3'RS)-N-(tert-butoxycarbonyl)-2-[2'-(ethoxycarbonyl)-3'-(2"-acetylthioethyl)cyclopropyl]glycinate (123 mg, 0.29 mmol) in 6N HCl (2.5 mL) was heated under reflux for 17 h. The solvent was then removed in vacuo and the resulting solid was washed with diethylether to give the corresponding hydrochloride salt of the title compound. After purification by ion exchange chromatography, 48 mg (74% yield) of (2SR,1'SR,2'SR,3'RS)-2-[3'-(2"-mercaptoethyl)-2'-carboxycyclopropyl]glycine were obtained as a white solid.

$^{13}$C-NMR (50 MHz, D$_2$O/KOD) δ: 182.7; 181.7; 55.9; 37.7; 31.4; 28.6; 27.3 and 25.5 ppm.

Example 7

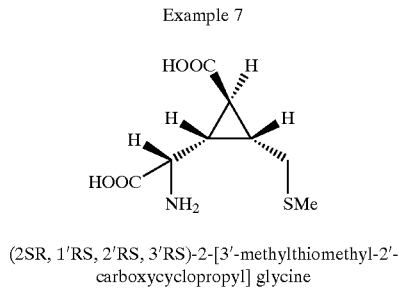

(2SR, 1'RS, 2'RS, 3'RS)-2-[3'-methylthiomethyl-2'-carboxycyclopropyl] glycine a) Ethyl (2SR,1'RS,2'RS,3'RS) N-(tert-butoxycarbonyl)-2-[2'-(ethoxycarbonyl)-3'-(methylthiomethyl)cyclopropyl]glycinate A mixture of tributylphosphine (1.16 mL, 4.72 mmol), dimethyl disulfide (0.31 mL, 3.54 mmol) and ethyl (2SR, 1'SR,2'RS,3'RS)-N-(tert-butoxycarbonyl)-2-[2'-(ethoxycarbonyl)-3'-(hydroxymethyl)cyclopropyl]glycinate (410 mg, 1.18 mmol) in dry tetrahydrofuran (8 mL), was stirred at 50° C. under argon for 20 h. Then, silicagel was added to the mixture and solvent was removed under reduced pressure. The resulting residue was purified by flash chromatography using hexane and diethylether 7:3 as eluent to afford 45 mg (10% yield) of the title compound.

$^1$H-NMR (200 MHz, CDCl$_3$) δ: 5.30 (bd, 1H); 4.25–3.93 (m, 5H); 2.90 (m, 1H); 2.49 (m, 1H); 2.12 (s, 3H); 1.76 (m, 3H); 1.40 (s, 9H) and 1.29–1.12 (m, 6H) ppm.

$^{13}$C-NMR (50 MHz, CDCl$_3$) δ: 172.4; 171.0; 155.2; 80.1; 62.1; 61.7; 52.0; 32.4; 29.9; 28.2 (3C); 27.3; 25.7; 15.5 and 14.5 (2C) ppm.

b) (2SR,1'RS,2'RS,3'RS)-2-[3'-(methylthiomethyl)-2'-carboxycyclopropyl]glycine A solution of ethyl (2SR,1'RS,2'RS,3'RS) N-(tert-butoxycarbonyl) -2-[2'-(ethoxycarbonyl)-3'-(methylthiomethyl)cyclopropyl]glycinate (55 mg, 0.14 mmol) in 6N HCl (2.5 mL) was heated under reflux for 16 h. The solvent was then removed in vacuo and the resulting solid was washed with diethyl ether to give the corresponding hydrochloride salt of the title compound. After purification by ion exchange chromatography, 26 mg (80% yield) of (2SR,1'RS, 2'RS,3'RS)-2-[3'-(methylthiomethyl)-2'-carboxycyclopropyl]glycine were obtained as a white solid.

$^1$H-NMR (200 MHz, D$_2$O/Py-d$_5$) δ: 3.07 (d, 1H, J=10 Hz); 2.60 (m, 1H); 1.88 (m, 1H); 1.45 (d, 5H) and 1.53 (t, 1H) ppm.

$^{13}$C-NMR (50 MHz, D$_2$O/Py-d$_5$) δ: 179.1; 172.6; 54.2; 31.6; 29.6; 26.3; 25.7 and 13.7 ppm.

Example 7

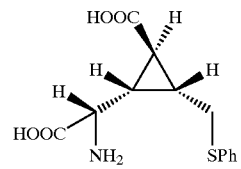

(2SR, 1'RS, 2'RS, 3'RS)-2-[3'-phenylthiomethyl-2'-carboxycyclopropyl] glycine a) Ethyl (2SR,1'RS,2'RS,3'RS) N-(tert-butoxycarbonyl)-2-[2'-(ethoxycarbonyl)-3'-(phenylthiomethyl)cyclopropyl]glycinate A mixture of tributylphosphine (0.26 mL, 1.04 mmol), diphenyl disulfide (170 mg, 0.78 mmol) and ethyl (2SR, 1'SR,2'RS,3'-RS)-N-(tert-butoxycarbonyl)-2-[2'-(ethoxycarbonyl)-3'-(hydroxymethyl) cyclopropyl]glycinate (90 mg, 0.26 mmol) in dry tetrahydrofuran (2 mL), was stirred at room temperature under argon for 20 h. Then, silicagel was added to the mixture and solvent was removed under reduced pressure. The resulting residue was purified by flash chromatography using hexane and ethyl acetate 4:1 as eluent to afford 80 mg (70% yield) of the title compound.

$^1$H-NMR (200 MHz, CDCl$_3$) δ: 7.25 (m, 5H); 5.20 (bd, 1H); 4.10 (m, 5H); 3.30 (dd, 1H); 2.85 (m, 1H); 1.75 (m, 3H); 1.40 (s, 9H) and 1.25 (m, 6H) ppm.

$^{13}$C-NMR (50 MHz, CDCl$_3$) δ: 172.3; 170.9; 155.2; 135.2; 130.5; 128.9; 126.6; 80.2; 61.7; 60.7; 52.1; 33.3; 30.2; 28.1 (3C); 26.9; 25.7 and 14.0 ppm.

IR (film): 3343, 3063, 2904, 1747, 1701, 1684, 1522, 1454, 1367, 1332, 1174, 1030 and 734 cm$^{-1}$.

Melting point: 90.0–92.5° C.

b) (2SR,1'RS,2'RS,3'RS)-2-[3'-(phenylthiomethyl)-2'-carboxycyclopropyl]glycine

A solution of ethyl (2SR,1'RS,2'RS,3'RS) N-(tert-butoxycarbonyl)-2-[2'-(ethoxycarbonyl)-3'-(phenylthiomethyl)cyclopropyl] glycinate (77 mg, 0.17 mmol) in 6N HCl (3 mL) was heated under reflux for 16 h. The solvent was then removed in vacuo and the resulting solid was washed with diethyl ether to give the corresponding hydrochloride salt of the title compound. After purification by ion exchange chromatography, 41 mg (83% yield) of (2SR,1'RS, 2'RS,3'RS)-2-[3'-(phenylthiomethyl)-2'-carboxycyclopropyl]glycine were obtained as a white solid.

$^1$H-NMR (200 MHz, D$_2$O/Py-d$_5$) δ: 6.99–6.47 (m, 5H); 3.11–3.01 (m, 2H), 2.32–2.21 (m, 1H); 1.57–1.41 (m, 2H) and 1.24–1.19 (t, 1H) ppm.

$^{13}$C-NMR (50 MHz, D$_2$O/Py-d$_5$) δ: 179.3; 173.0; 135.4; 129.6; 129.4; 126.3; 54.9; 32.9; 29.4; 27.7 and 25.8 ppm.

IR (film): 3059, 1716, 1678, 1585, 1514, 1385, 1184, 1014 and 897 cm$^{-1}$.

Melting point: 201° C.

Example 9

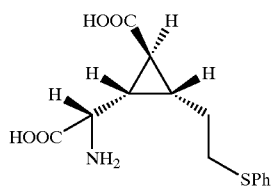

(2SR, 1'SR, 2'RS, 3'RS)-2-[(3'-(2''-phenylthioethyl)-2'-carboxycyclopropyl]glycine a) Ethyl (2SR,1'SR,2'SR,3'RS)-N-(tert-butoxycarbonyl)-2-[2'-(ethoxycarbonyl)-3'-(2''-phenylthioethyl)cyclopropyl]glycinate A mixture of tributylphosphine (0.52 mL, 2.12 mmol), diphenyl disulfide (346 mg, 1.58 mmol) and ethyl (2SR, 1'SR,2'SR,3'RS)-N-(tert-butoxycarbonyl)-2-[2'-(ethoxycarbonyl)-3'-(2''-hydroxyethyl)cyclopropyl] glycinate (190 mg, 0.53 mmol) in dry tetrahydrofuran (5.5 mL), was stirred at room temperature under argon for 20 h. Then, silicagel was added to the mixture and solvent was removed under reduced pressure. The resulting residue was purified by flash chromatography using hexane and ethyl acetate 4:1 as eluent to afford 186 mg (78% yield) of the title compound.

$^1$H-NMR (200 MHz, CDCl$_3$) δ: 7.32–7 30 (m, 5H); 5.20 (bd, 1H); 4.23–4.04 (m, 4H); 3.90 (bs, 1H); 3.06 (t, 2H); 2.06 (m, 1H); 1.71–1.66 (m, 4H); 1.43 (s, 9H) and 1.27 (m, 6H) ppm.

$^{13}$C-NMR (50 MHz, CDCl$_3$) δ: 172.8; 171.1; 155.2; 136.1; 130.6; 129.3; 128.0; 126.0; 80.1; 61.6; 60.7; 52.1; 33.1; 30.1; 28.1 (3C); 27.8; 26.8; 25.5; 14.1 and 13.9 ppm.

b) (2SR,1'SR,2'SR,3'RS)-2-[(3'-(2''-phenylthioethyl)-2'-carboxycyclopropyl]glycine A solution of ethyl (2SR,1'SR,2'SR,3'RS) N-(tert-butoxycarbonyl)-2-[2'-(ethoxycarbonyl)-3'-(2''-phenylthioethyl)cyclopropyl]glycinate (186 mg, 0.41 mmol) in 6N HCl (3.3 mL) was heated under reflux overnight. The solvent was then removed in vacuo and the resulting solid was washed with diethyl ether to give the corresponding hydrochloride salt of the title compound. After purification by ion exchange chromatography, 60 mg (49% yield) of (2SR,1'SR,2'SR,3'RS)-2-[3'-(2''-phenylthioethyl)-2'-carboxycyclopropyl]glycine were obtained as a white solid.

$^1$H-NMR (200 MHz, D$_2$O/Py-d$_5$) δ: 6.56–6.44 (m, 5H); 2.95 (d, 1H), 2.50–2.36 (m, 2H); 1.53 (m, 2H); 1.30 (m, 1H); 1.14 (m, 1H) and 1.05 (m, 1H) ppm.

$^{13}$C-NMR (50 MHz, D$_2$O/Py-d$_5$) δ: 179.0; 171.7; 136.2; 128.5; 127.7; 125.1; 123.4; 54.5; 31.7; 28.0; 27.4; 26.8 and 25.5 ppm.

IR (film): 3132, 3020, 2955, 2914, 1730, 1626, 1529, 1481, 1387, 1358, 1329, 1219 and 746 cm$^{-1}$.

Example 10

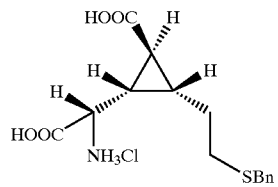

(2SR, 1'SR, 2'SR, 3'RS)-2-[(3'-(2''-benzylthioethyl)-2'-carboxycyclopropyl]glycine hydrochloride a) Ethyl (2SR,1'SR,2'SR,3'RS)-N-(tert-butoxycarbonyl)-2-[2'-(ethoxycarbonyl)-3'-(2''-benzylthioethyl)cyclopropyl]glycinate To a mixture of tributylphosphine (0.70 mL, 2.83 mmol), dibenzyl disulfide (522 mg, 2.12 mmol) and ethyl (2SR, 1'SR,2'SR,3'RS)-N-(tert-butoxycarbonyl)-2-[2'-(ethoxycarbonyl)-3'-(2''-hydroxyethyl)cyclopropyl] glycinate (254 mg, 0.71 mmol) in dry tetrahydrofuran (7 mL), N,N-dimethylamino-pyridine g(8.5 mg, 0.07 mmol) was added and the reaction mixture was stirred at 75° C. under argon for 24 h. Then, silica gel was added to the mixture and solvent was removed under reduced pressure. The resulting residue was purified by flash chromatography using hexane and ethyl acetate 3:1 as eluent to afford 59 mg (18% yield) of the title compound.

$^1$H-NMR (200 MHz, CDCl$_3$) δ: 7.32–7.26 (m, 5H); 5.19 (bd, 1H); 4.26–4.13 (m, 5H); 4.12 (m, 1H); 3.88 (m, 1H); 2.55 (t, 2H); 2.16 (s, 2H); 1.99–1.87 (m,1H); 1.84(m,1H); 1.69 (m,1H); 1.45 (s, 9H) and 1.25 (m, 6H) ppm.

$^{13}$C-NMR (50 MHz, CDCl$_3$) δ: 172.9; 171.1; 155.2; 138.2; 129.2; 128.8; 128.4; 126.9; 80.1; 61.6; 60.6; 52.1; 36.3; 30.1; 29.6; 29.3; 28.2; 28.0 (3C); 27.0 and 14.0 ppm.

b) (2SR,1'SR,2'SR,3'RS)-2-[3'-(2"-benzylthioethyl)-2'-carboxycyclopropyl]glycine hydrochloride A solution of ethyl (2SR,1'SR,2'SR,3'RS) N-(tert-butoxycarbonyl)-2-[2'-(ethoxycarbonyl)-3'-(2"-benzylthioethyl)cyclopropyl]glycinate (71 mg, 0.15 mmol) in 2N HCl (3.7 mL) was heated under reflux overnight. The solvent was then removed in vacuo and the resulting solid was washed with diethyl ether to give 41 mg (77% yield) of (2SR,1'SR,2'SR,3'RS)-2-[3'-(2"-benzylthioethyl)-2'-carboxycyclopropyl]glycine hydrochloride as a white solid.

$^1$H-NMR (200 MHz, CD$_3$OD) δ: 7.34–7.20 (m, 5H); 3.75 (s, 2H); 3.64 (d, 1H); 2 61 (t, 2H), 2.12 (m, 1H) and 1.84–1.50 (m, 4H) ppm.

$^{13}$C-NMR (50 MHz, CD$_3$OD) δ: 175.4; 170.6; 140.0; 129.9; 129.4; 127.9; 53.3; 37.0; 31.5; 28.9; 28.2; 27.7 and 26.1 ppm.

Example 11

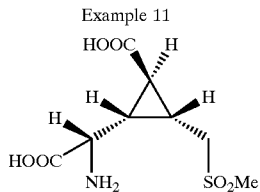

(2SR, 1'RS, 2'RS, 3'RS)-2-[3'-methylsulfonylmethyl-2'-carboxycyclopropyl]glycine a) Ethyl (2SR,1'RS,2'RS,3'RS) N-(tert-butoxycarbonyl)-2-[2'-(ethoxycarbonyl)-3'-(methylsulfonylmethyl)cyclopropyl]glycinate To a solution of ethyl (2 SR,1'RS,2'RS,3'RS) N-(tert-butoxycarbonyl)-2-[2'-(ethoxycarbonyl)-3'-(methylthiomethyl)cyclopropyl]glycinate (54 mg, 0.14 mmol) in anhydrous dichloromethane (1 mL) at 0° C. under a nitrogen atmosphere, m-chloroperoxybenzoic acid (71 mg, 0.28 mmol) was added. The mixture was stirred for 1 h at this temperature. Then, the residue was diluted with dichloromethane and washed with a 15% aqueous solution of sodium bisulfite and with a saturated aqueous solution of sodium bicarbonate. The organic phase was dried over magnesium sulfate, and the solvent removed under reduced pressure. The residue was purified by flash chromatography using hexane and ethyl acetate 1:1 as eluent to afford 42 mg (72% yield) of the title compound.

$^1$H-NMR (200 MHz, CDCl$_3$) δ: 5.33 (bd, 1H, J=8.4 Hz); 4.27–4.06 (dq, 4H); 3.93 (t, 1H, J=8.9 Hz); 3.56–3.48 (dd, 1H, J=3.2 and 14.7 Hz); 3.03 (m, 1H); 2.93 (s, 3H); 2.04–1.78 (m, 3H); 1.40 (s, 9H) and 1.31–1.18 (dt, 6H) ppm.

$^{13}$C-NMR (50 MHz, CDCl$_3$) δ: 171.2; 170.4; 155.3; 80.4; 62.2; 61.5; 53.7; 52.0; 40.3; 28.1 (3C); 27.7; 24.9 and 19.0 ppm.

b) (2SR,1'RS,2'RS,3'RS)-2-[3'-(methylsulfonylmethyl)-2'-carboxycyclopropyl]glycine A solution of ethyl (2SR,1'RS,2'RS,3'RS) N-(tert-butoxycarbonyl)-2-[2'-(ethoxycarbonyl)-3'-(methylsulfonylmethyl)cyclopropyl]glycinate (42 mg, 0.10 mmol) in 6N HCl (2 mL) was heated under reflux for 16 h. The solvent was then removed in vacuo and the resulting solid was washed with diethylether to give the corresponding hydrochloride salt of the title compound. This hydrochloride was dissolved in MeOH (1 mL) and propylene oxide (3 mL) was added. The mixture was stirred overnight at room temperature and the resulting insoluble solid was filtered and washed with diethylether to give 19 mg (74% yield) of (2SR,1'RS,2'RS,3'RS)-2-[3'-(methylsulfonylmethyl)-2'-carboxycyclopropyl]-glycine as a white solid.

$^1$H-NMR (200 MHz, D$_2$O/Py-d$_5$) δ: 3.45(d, 1H); 3.10–2.50 (m, 3H); 2.54 (s, 3H) and 1.58 (bs, 2H) ppm.

$^{13}$C-NMR (50 MHz, D$_2$O/Py-d$_5$) δ: 178.2; 172.6; 54.7; 53.8; 39.7; 28.7; 25.0 and 19.0 ppm.

Example 12

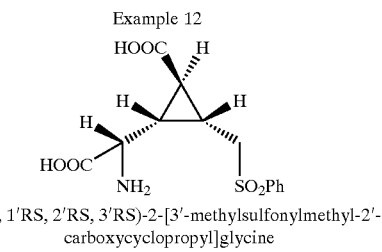

(2SR, 1'RS, 2'RS, 3'RS)-2-[3'-methylsulfonylmethyl-2'-carboxycyclopropyl]glycine a) Ethyl (2SR,1'RS,2'RS,3'RS) N-(tert-butoxycarbonyl)-2-[2'-(ethoxycarbonyl)-3'-(phenylsulfonylmethyl)cyclopropyl]glycinate To a solution of ethyl (2 SR,1'RS,2' RS,3' RS) N-(tert-butoxycarbonyl)-2-[2'-(ethoxycarbonyl)-3'-(phenylthiomethyl)cyclopropyl]glycinate (50 mg, 0.11 mmol) in anhydrous dichloromethane (1 mL) at 0° C. under nitrogen atmosphere, m-chloroperoxybenzoic acid (54.3 mg, 0.22 mmol) was added. The mixture was stirred for 3h at this temperature. Then, the residue was diluted with dichloromethane and washed with a 15% aqueous solution of sodium bisulfite and with a saturated aqueous solution of sodium bicarbonate. The organic phase was dried over magnesium sulfate, and the solvent removed under reduced pressure. The residue was purified by flash chromatography using hexane and ethyl acetate 2:1 as eluent to afford 42 mg (78% yield) the title compound.

$^1$H-NMR (200 MHz, CDCl$_3$) δ: 8.33 (d, 2H, J=6 Hz); 8.11–7.80 (m, 3H); 5.27(bd, 1H, J=8 Hz); 4.31–4.04 (dq, 4H); 3.88 (t, 1H); 3.78–3.69 (dd, 1H); 3.08 (m, 1H); 1.84–1.59 (m,3H); 1.44 (s, 9H) and 1.36–1.22 (dt, 6H) ppm.

$^{13}$C-NMR (50 MHz, CDCl$_3$) δ: 171.3; 170.4; 155.1; 138.4; 133.9; 129.3; 128.3; 80.5; 62.0; 61.8; 55.2; 52.0; 28.1 (3C); 27.9; 24.9; 20.0 and 14.1 (2C) ppm.

IR (film): 3408, 3358, 2982, 1736, 1724, 1697, 1512, 1371, 1294, 1250, 1178, 1145, 1086 and 1020 cm$^{-1}$.

Melting point: 101–102° C.

b) (2SR,1'RS,2'RS,3'RS)-2-[3'-(phenylsulfonylmethyl)-2'-carboxycyclopropyl]glycine A solution of ethyl (2SR,1'RS,2'RS,3'RS) N-(tert-butoxycarbonyl)-2-[2'-(ethoxycarbonyl)-3'-(phenylsulfonylmethyl)cyclopropyl] glycinate (60 mg, 0.12 mmol) in 6N HCl (2 mL) was heated under reflux for 16 h. The solvent was then removed in vacuo and the resulting solid was washed with diethylether to give the corresponding hydrochloride salt of the title compound. After purification by ion exchange chromatography, 24 mg (60% yield) of (2SR,1'RS,2'RS,3'RS)-2-[3'-(phenylsulfonylmethyl)-2'-carboxycyclopropyl]glycine were obtained as a white solid.

$^1$H-NMR (200 MHz, D$_2$O/Py-d$_5$) δ: 7.40 (d, 2H); 7.15(m, 3H); 3.65 (d, 1H); 3.45(m, 1H); 2.90(m, 1H) and 1.40(m, 3H) ppm.

¹³C-NMR (50 MHz, D₂O/Py-d₅) δ: 178.1; 172.7; 136.6; 134.7; 129.8; 128.1; 55.3; 54.7; 28.6; 25.0 and 19.3 ppm.

Example 13

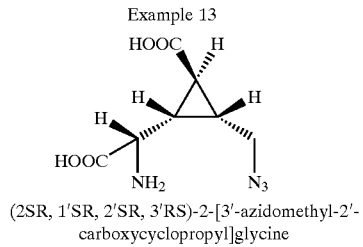

(2SR, 1'SR, 2'SR, 3'RS)-2-[3'-azidomethyl-2'-carboxycyclopropyl]glycine a) Ethyl (2SR,1'SR,2'SR,3'RS)-N-(tert-butoxycarbonyl)-2-[2'-(ethoxycarbonyl)-3'-(azidomethyl)cyclopropyl]glycinate Diethyl azodicarboxylate (1.08 mmol, 0.17 mL) was added dropwise to a solution of triphenylphosphine (1.08 mmol, 0.285 g) in anhydrous tetrahydrofuran (20 mL) at 20° C. under a nitrogen atmosphere and the reaction mixture was stirred at the same temperature for 10 min. A solution of ethyl (2SR,1'SR,2'RS,3'RS)-N-(tert-butoxycarbonyl)-2-[2'-(ethoxycarbonyl)-3'-hydroxy-methylcyclopropyl]glycinate (0.87 mmol, 300 mg) in tetrahydrofuran (5 mL) was then added and the resulting mixture stirred for 10 min at −20° C. After that time, diphenylphosphoryl azide (1.13 mmol, 0.25 mL) was added to the reaction mixture at the same temperature and then allowed to react at room temperature for 3 days. The reaction mixture was quenched with water and the organic phase extracted with ethyl acetate (2×25 mL). The combined organic layers were dried over magnesium sulfate, filtered and concentrated under vacuo. The product was purified by column chromatography using hexane and ethyl acetate 4:1 as eluent to give 250 mg (78% yield) of ethyl (2SR,1'SR, 2'SR,3'RS)-N-(tert-butoxycarbonyl)-2-[2'-(ethoxycarbonyl)-3'-(azidomethyl)-cyclopropyl] glycinate as a colorless oil.

1H-NMR (CDCl₃, 200 MHz) δ ppm): 5.2 (1H, d, J=8 Hz), 4.3–3.9 (5H, m), 3.6 (1H, dd, J=13 and 5 Hz), 3.3 (1H, dd, J=13 and 7 Hz), 1.9–1.7 (3H, m), 1.4 (9H, s), 1.3–1.2 (6H, m)

¹³C-NMR (CDCl₃, 50 MHz) δ ppm): 172.1, 170.7, 155.2, 80.2, 61.8, 61.0, 52.0, 49.4, 29.0, 28.1, 25.4, 24.0, 14.0 b) (2SR,1'SR,2'SR,3'RS)-2-(3'-azidomethyl-2'-carboxycyclopropyl)glycine

To a solution of ethyl (2SR,1'SR,2'SR,3'RS)-N-(tert-butoxycarbonyl)-2-[2'-(ethoxycarbonyl)-3'-azidomethylcyclopropyl]glycinate (75 mg, 0.20 mmol) in tetrahydrofuran (2 mL) at room temperature, a 2.5M solution of LiOH.H₂O in H₂O (3.2 mL, 8 mmol) was added and mixture was stirred at room temperature overnight. The following day, ethyl acetate was added, organic layer separated and aqueous layer washed with ethyl acetate (2×). The aqueous layer was acidified to pH 1 with 1N HCl and extracted in ethyl acetate (5×). The combined organic layers were dried over magnesium sulfate, filtered and concentrated under reduced pressure. The resulting residue was dissolved in a 1N solution of HCl in ethyl acetate (1.6 mL) and the solution was stirred overnight at room temperature. Then, it was concentrated under vacuum and the solid was washed with diethyl ether. The resulting hydrochloride salt of the title compound was dissolved in methanol (2 mL) and propylene oxide (5 mL) was added. The mixture was stirred overnight and the precipitate was filtered and washed with diethyl ether to give 32 mg (73% yield) of (2SR,1'SR,2'SR, 3'RS)-2-(3'-azidomethyl-2'-carboxycyclopropyl)glycine as a white solid.

¹H-NMR (D₂O, 200 MHz) δ ppm): 3.6 (1H, dd, J=13, 5 Hz), 3.3 (1H, d, J=10 Hz), 3.2 (1H, dd, J=13, 8 Hz), 1.9–1.7 (3H, m)

¹³C-NMR (D₂O/MeOH-d₄, 50 MHz) δ ppm): 177.4, 173.2, 54.7, 50.1, 27.4, 26.9, 25.7

Example 14

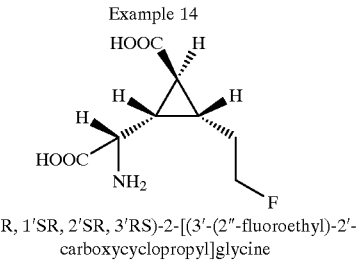

(2SR, 1'SR, 2'SR, 3'RS)-2-[(3'-(2''-fluoroethyl)-2'-carboxycyclopropyl]glycine a) Ethyl (2SR,1'SR,2'SR,3'RS)-N-(tert-butoxycarbonyl)-2-[2'-(ethoxycarbonyl)-3'-(2''-fluoroethyl)cyclopropyl]glycinate To a solution of ethyl (2SR,1'SR,2'SR,3'RS)-N-(tert-butoxycarbonyl)-2-[2'-(ethoxycarbonyl)-3'-(2''-hydroxyethyl)cyclopropyl] glycinate (0.84 mmol, 300 mg) in dichloromethane (15 mL) at room temperature, (diethylamino)sulfur trifluoride (1.26 mmol, 0.17 mL) was added. The resulting mixture was stirred for 1.5 h and then quenched with water (5 mL). The layers were separated and the aqueous phase was extracted with dichloromethane (3×10 mL). The combined organic layers were dried over magnesium sulfate, filtered and concentrated under vacuum. The product was purified by column chromatography using a hexane and ethyl acetate 4:1 as eluent to afford 160 mg (53% yield) of ethyl (2SR,1'SR,2'SR,3'RS)-N-(tert-butoxycarbonyl)-2-[2'-(ethoxycarbonyl)-3'-(2''-fluoroethyl) cyclopropyl] glycinate.

¹H-NMR (CDCl₃, 200 MHz) δ ppm): 5.3 (1H, d, J=7 Hz), 4.7–4.4 (2H, dt, J=47, 6 Hz), 4.2 (2H, q, J=7 Hz), 4.1 (2H, q, J=7 Hz), 3.9 (1H, m), 2.3–1.7 (5H, m), 1.4 (9H, s), 1.3–1.2 (6H, m)

¹³C-NMR (CDCl₃, 50 MHz) δ ppm): 172.7, 171.0, 155.2, 82.8 (d, J=167 Hz), 80.1, 61.6, 60.6, 52.1, 29.2 (d, J=14 Hz), 28.7, 28.1, 24.4, 23.7 (d, J=7 Hz), 14.0, 13.9 b) (2SR,1'SR,2'SR,3'RS)-2-(3'-(2''-fluoroethyl)-2'-carboxycyclopropyl)glycine

To a solution of ethyl (2SR,1'SR,2'SR,3'RS)-N-(tert-butoxycarbonyl)-2-[2'-(ethoxycarbonyl)-3'-(2''-fluoroethyl) cyclopropyl]glycinate (150 mg, 0.41 mmol) in tetrahydrofuran (4.1 mL), a 2.5M solution of LiOH.H₂O (340 mg, 8.2 mmol) in H₂O (3.4 mL) was added and the mixture was stirred at room temperature overnight. The following day, ethyl acetate (2 mL) was added, organic layer separated and aqueous layer washed with ethyl acetate (3×2 mL). The aqueous layer was acidified to pH 1 with 1N HCl and extracted in ethyl acetate (5×10 mL). The combined organic layers were dried over magnesium sulfate, filtered and concentrated under vacuum. The residue was dissolved in a 1N solution of HCl in ethyl acetate (3.3 mL, 3.3 mmol) and the solution was stirred overnight at room temperature. It was concentrated under vacuum and the solid was washed with diethyl ether to give the corresponding hydrochloride salt of the title compound. After purification by ion exchange chromatography, 70 mg (83% yield) of (2SR,1'SR,2'SR, 3'RS)-2-(3'-(2"-fluoroethyl)-2'-carboxycyclopropyl) glycine were obtained as a white solid.

$^1$H-NMR (D$_2$O, 200 MHz) δ ppm): 4.5–4.3 (2H, dt, J=47, 5 Hz), 3.3 (1H, d, J=10 Hz), 2.2–1.9 (1H, m), 1.7–1.3 (4H, m)

$^{13}$C-NMR (D$_2$O/py-d$_5$, 50 MHz) δ ppm): 180.4, 173.2, 147.0, 84.3 (d, J=160 Hz), 54.6, 28.5 (d, J=15 Hz), 27.9, 25.8, 22.7 (d, J=5 Hz).

Example 15

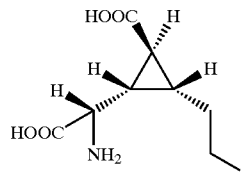

(2SR, 1'SR, 2'SR, 3'RS)-2-[(3'-(2"-chloroethyl)-2'-carboxycyclopropyl]glycine a) Ethyl (2SR,1'SR,2'SR,3'RS)-N-(tert-butoxycarbonyl)-2-[2'-(ethoxycarbonyl)-3'-(2"-chloroethyl)cyclopropyl]glycinate To a solution of ethyl (2SR,1'SR,2'SR,3'RS)-N-(tert-butoxycarbonyl)-2-[2'-(ethoxycarbonyl)-3'-(2"-hydroxyethyl)cyclopropyl]glycinate (0.84 mmol, 300 mg) in anhydrous dimethylformamide (6 mL), triphenylphosphine (2.5 mmol, 0.65 g) and carbon tetrachloride (6 mL) were added at room temperature. The resulting mixture was stirred overnight and then water (3 mL) and ethyl acetate (20 mL) were added. The organic layer was separated and the aqueous layer was extracted with ethyl acetate (3×10 mL). The combined organic layers were washed with water (5×10 mL), dried over magnesium sulfate, filtered and concentrated under vacuum. The residue was purified by column chromatography using hexane and ethyl acetate 4:1 as eluent to afford 220 mg (58% yield) of ethyl (2SR, 1'SR,2'SR, 3'RS)-N-(tert-butoxycarbonyl)-2-[2'-(ethoxycarbonyl)-3'-(2"-chloroethyl)cyclopropyl]glycinate.

$^1$H-NMR (CDCl$_3$, 200 MHz) δ ppm): 5.3 (1H, d, J=8 Hz), 4.2 (2H, d, J=7 Hz), 4.1 (2H, d, J=7 Hz), 3.9 (1H, m), 3.6 (2H, t, J=6 Hz), 2.3–2.1 (1H, m), 1.9–1.6 (4H, m), 1.4 (9H, s), 1.3–1.2 (6H, m)

$^{13}$C-NMR (CDCl$_3$, 50 MHz) δ ppm): 172.6, 170.9, 155.2, 80.0, 61.6, 60.6, 52.1, 43.6, 31.0, 29.5, 27.7, 25.1, 24.5, 14.0, 13.9 b) Synthesis of (2SR,1'SR,2'SR,3'RS)-2-(3'-(2"-chloroethyl)-2'-carboxycyclopropyl)glycine hydrochloride To a solution of ethyl (2SR,1'SR,2'SR,3'RS)-N-(tert-butoxycarbonyl)-2-[2'-(ethoxycarbonyl)-3'-(2"-chloroethyl) cyclopropyl]glycinate (200 mg, 0.53 mmol) in tetrahydrofuran (5.3 mL), a 0.25 M solution of LiOH.H$_2$O (66 mg, 1.59 mmol) in H$_2$O (6.4 mL) was added and the mixture was stirred at room temperature for three days. Then, ethyl acetate (3 mL) was added, the organic layer was separated and the aqueous layer was washed with ethyl acetate (3×3 mL). The aqueous layer was acidified to pH 1 with 1N HCl and extracted in ethyl acetate (5×10 mL). The combined organic layers were dried over magnesium sulfate, filtered and concentrated under vacuum. The residue was dissolved in a 1N solution of HCl in EtOAc (4.2 mL, 4.2 mmol) and the solution was stirred overnight at room temperature. The resulting mixture was concentrated under vacuum and the solid was washed with diethyl ether to give the corresponding hydrochloride salt of the title compound. After purification by ion exchange chromatography, 80 mg (68% yield) of (2SR,1'SR,2'SR, 3'RS)-2-(3'-(2"-chloroethyl)-2'-carboxy cyclopropyl)glycine were obtained as a white solid.

$^1$H-NMR (D$_2$O, 200 MHz) δ ppm): 3.5 (2H, t, J=10 Hz), 3.3 (1H, d, J=10 Hz), 2.1–1.9 (1H, m), 1.7–1.3 (4H, m).

$^{13}$C-NMR (D$_2$O/py-d$_5$, 50 MHz) δ ppm): 179.3, 172.7, 54.5, 44.2, 30.6, 27.8, 26.1, 23.9.

Example 16

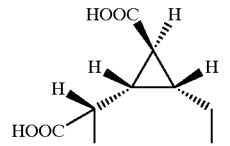

(2SR, 1'SR, 2'SR, 3'RS)-2-[3'-acetylaminomethyl-2'-carboxycyclopropyl]glycine a) Ethyl (2SR,1'SR,2'SR,3'RS)-N-(tert-butoxycarbonyl)-2-[2'-(ethoxycarbonyl)-3'-(acetylaminomethyl)cyclopropyl]glycinate To a solution of ethyl (2SR,1'SR,2'SR,3'RS)-N-(tert-butoxycarbonyl)-2-[2'-(ethoxycarbonyl)-3'-(azidomethyl) cyclopropyl]glycinate (500 mg, 1.35 mmol) in ethanol (15 mL), acetic anhydride (0.3 mL, 2.7 mmol) and 10% palladium on activated carbon (90 mg) were added. The resulting mixture was stirred at room temperature under hydrogen atmosphere for 2 hours. Then, mixture was filtered through celite and concentrated under reduced pressure. The resulting residue was purified by column chromatography using hexane and ethyl acetate 1:1 as eluent to afford 375 mg (72% yield) of ethyl (2SR,1'SR, 2'SR,3'RS)-N-(tert-butoxycarbonyl)-2-[2'-(ethoxycarbonyl)-31-(acetylaminomethyl)cyclopropyl]glycinate.

$^1$H-NMR (CDCl$_3$, 200 MHz) δ ppm): 6.6 (1H, broad s), 5.3 (1H, d, J=8 Hz), 4.3–3.9 (6H, m), 2.9–2.8 (1H, m), 1.9 (3H, s), 1.9–1.7 (3H, m), 1.4 (9H, s), 1.3–1.1 (6H, m)

$^{13}$C-NMR (CDCl$_3$, 50 MHz) δ ppm): 172.1, 171.6, 169.9, 155.5, 80.4, 62.1, 60.9, 52.4, 37.7, 28.9, 28.1, 26.6, 23.2, 14.0.

b) (2SR,1'SR,2'SR,3'RS)-2-(3'-acetylaminomethyl-2'-carboxycyclopropyl)glycine

To a solution of ethyl (2SR,1'SR,2'SR,3'RS)-N-(tert-butoxycarbonyl)-2-[2'-(ethoxycarbonyl)-3'-(acetyl-aminomethyl)cyclopropyl] glycinate (60 mg, 0.15 mmol) in tetrahydrofuran (1.5 mL), a 2.5M solution of LiOH.H$_2$O (252 mg, 6.0 mmol) in H$_2$O (2.4 mL) was added and the mixture was stirred at room temperature overnight. The following day ethyl acetate (1 mL) was added, the organic layer was separated and the aqueous layer was washed with ethyl acetate (3×1 mL). The aqueous layer was acidified to pH 1 with 1N HCl and extracted with ethyl acetate (5×5 mL). The combined organic layers were dried over magnesium sulfate, filtered and concentrated under vacuum. The residue was dissolved in a 1N solution of HCl in ethyl acetate (1.75 mL, 1.75 mmol) and the solution was stirred overnight at room temperature. It was concentrated under vacuum and the solid was washed with diethyl ether to give the corresponding hydrochloride salt of the title compound. This hydrochloride was dissolved in MeOH (1 mL) and propylene oxide (3 mL) was added. The mixture was stirred overnight at room temperature and the resulting insoluble solid was filtered and washed with diethyl ether to give 10 mg of (2SR,1'SR,2'SR,3'RS)-2-(3'-acetylaminomethyl-2'-carboxycyclopropyl)glycine (30% yield) as a white solid.

$^1$H-NMR (D$_2$O/MeOH-d$_4$, 200 MHz) δ ppm): 3.7 (1H, dd, J=14, 6 Hz), 3.2 (1H, d, J=10 Hz), 3.0 (1H, dd, J=14, 7 Hz), 1.9 (3H, s), 1.8–1.6 (3H, m)

$^{13}$C-NMR (D$_2$O/MeOH-d$_4$, 50 MHz) δ ppm): 175.4, 172.3, 171.4, 52.8, 36.9, 26.0, 25.2, 23.5, 21.0

Example 17

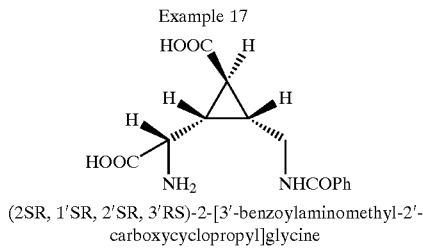

(2SR, 1'SR, 2'SR, 3'RS)-2-[3'-benzoylaminomethyl-2'-carboxycyclopropyl]glycine a) Ethyl (2SR,1'SR,2'SR,3'RS)-N-(tert-butoxycarbonyl)-2-[2'-(ethoxycarbonyl)-3'-(benzoylaminomethyl)-cyclopropyl]glycinate To a solution of ethyl (2SR,1'SR,2'SR,3'RS)-N-(tert-butoxycarbonyl)-2-[2'-(ethoxycarbonyl)-3'-(azidomethyl) cyclopropyl]glycinate (500 mg, 1.35 mmol) in ethyl acetate (15 mL), benzoic anhydride (0.23 mL, 2.0 mmol) and platinium (IV) oxide (61 mg, 0.27 mmol) were added. The resulting mixture was stirred at room temperature under hydrogen atmosphere for 2 hours. Then, the mixture was filtered through celite and concentrated under reduced pressure. The resulting residue was purified by column chromatography using hexane and ethyl acetate 1:1 as eluent to afford 363 mg (65% yield) of ethyl (2SR, 1'SR,2'SR,3'RS)-N-(tert-butoxycarbonyl)-2-[2'-(ethoxycarbonyl)-31-(benzoylaminomethyl)cyclopropyl]glycinate.

$^1$H-NMR (CDCl$_3$, 200 MHz) δ ppm): 7.9 (2H, m), 7.6–7.4 (3H, m), 5.3 (1H, d, J=8 Hz), 4.5 (1H, m), 4.4–4.1 (5H, m), 3.1–3.0 (1H, m), 2.0–1.8 (3H, m), 1.5 (9H, s), 1.3–1.2 (6H, m)

$^{13}$C-NMR (CDCl$_3$, 50 MHz) δ ppm): 172.1, 171.7, 167.0, 155.4, 134.2, 131.3, 128.4, 127.0, 80.5, 62.4, 61.0, 52.5, 38.0, 28.9, 28.2, 26.6, 23.0, 14.0 b) (2SR,1'SR,2'SR,3'RS)-2-(3'-benzoylaminomethyl-2'-carboxycyclopropyl)glycine

To a solution of ethyl (2SR,1'SR,2'SR,3'RS)-N-(tert-butoxycarbonyl)-2-[2'-(ethoxycarbonyl)-3'-(benzoylaminomethyl)cyclopropyl] glycinate (50 mg, 0.11 mmol) in tetrahydrofuran (1.5 mL), a 2.5M solution of LiOH.H$_2$O (185 mg, 4.4 mmol) in H$_2$O (1.75 mL) was added and the mixture was stirred at room temperature overnight. The following day ethyl acetate (1 mL) was added, the organic layer separated and the aqueous layer was washed with ethyl acetate (3×1 mL). The aqueous layer was acidified to pH 1 with 1N HCl and extracted with ethyl acetate (5×3 mL). The combined organic layers were dried over magnesium sulfate, filtered and concentrated under vacuum. The residue was dissolved in a 1N solution of HCl in ethyl acetate (1 mL, 1 mmol) and the solution was stirred overnight at room temperature. It was then concentrated under vacuum and the solid was washed with diethyl ether to give the corresponding hydrochloride salt of the title compound. After purification by ion exchange chromatography, 8.0 mg (25% yield) of (2SR,1'SR,2'SR, 3'RS)-2-(3'-benzoylaminomethyl-2'-carboxycyclopropyl) glycine were obtained as a white solid.

$^1$H-NMR (D$_2$O/py-d$_5$, 200 MHz) δ ppm): 7.6–7.1 (5H, m), 3.8 (1H, dd, J=14, 5 Hz), 3.3 (1H, d, J=10 Hz), 2.7 (1H, dd, J=14, 8 Hz), 1.7–1.5 (3H, m)

$^{13}$C-NMR (D$_2$O/py-d$_5$, 50 MHz) δ ppm): 179.7, 173.3, 169.1, 133.2, 132.2, 128.8, 127.3, 54.6, 38.8, 27.1, 26.4, 25.0

Example 18

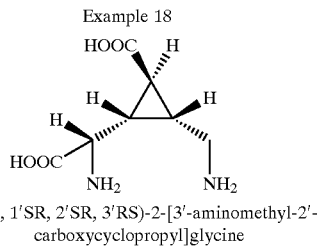

(2SR, 1'SR, 2'SR, 3'RS)-2-[3'-aminomethyl-2'-carboxycyclopropyl]glycine a) (2SR,1'SR,2'SR,3'RS)-2-[3'-aminomethyl-2'-carboxycyclopropyl]glycine A solution of ethyl (2SR,1SR,2'SR,3'RS)-N-(tert-butoxycarbonyl)-2-[2'-(ethoxycarbonyl)-3-(acetylaminomethyl)cyclopropyl]glycinate (300 mg, 0.77 mmol) in 2N HCl (5 mL) was stirred at room temperature for 24 hours and then heated at 55$^2$C for 60 hours. Solvent was removed under vacuum to give the corresponding hydrochloride salt of the title compound. After purification by ion exchange chromatography, 58 mg (40% yield) of (2SR,1'SR, 2'SR, 3'RS)-2-(3'-aminomethyl-2'-carboxycyclopropyl) glycine were obtained as a white solid.

$^1$H-NMR (D$_2$O/py-d$_5$, 200 MHz) δ ppm): 3.3 (1H, m), 3.3 (1H, d, J=11 Hz), 2.7 (1H, dd, J=13, 10 Hz), 1.8–1.5 (3H, m)

$^{13}$C-NMR (D$_2$O/py-d$_5$, 50 MHz) 8ppm): 178.3, 172.7, 53.8, 38.2, 27.0, 25.6, 21.8

Example 19

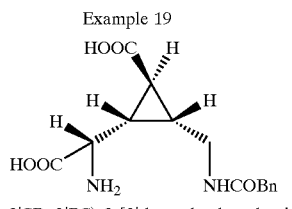

(2SR, 1'SR, 2'SR, 3'RS)-2-[3'-benzylcarbonylaminomethyl-2'-carboxycyclopropyl]glycine a) Ethyl (2SR,1'SR,2'SR,3'RS)-N-(tert-butoxycarbonyl)-2-[2'-(ethoxycarbonyl)-3'-(benzylcarbonylaminomethyl)cyclopropyl]glycinate To a solution of ethyl (2SR,1'SR,2'SR,3'RS)-N-(tert-butoxycarbonyl)-2-[2'-(ethoxycarbonyl)-3'-(azidomethyl) cyclopropyl]glycinate (100 mg, 0.27 mmol) in ethyl acetate (4 mL), platinium (IV) oxide (0.054 mmol, 12 mg) was added and the mixture was allowed to react at room temperature under a hydrogen atmosphere for 4 hours. Then, the phenylacetyl chloride (0.072 mL, 0.54 mmol) was added and the reaction mixture was stirred at room temperature under nitrogen atmosphere overnight. The following day, the mixture was filtered through celite and concentrated under vacuum. The residue was purified by column chromatography using a gradient from hexane and ethyl acetate 6:4 to ethyl acetate as eluent to afford 55 mg (45% yield) of ethyl (2SR,1'SR,2'SR,3'RS)-N-(tert-butoxycarbonyl)-2-[2'-(ethoxycarbonyl)-3'-(benzylcarbonylaminomethyl) cyclopropyl]-glycinate.

$^1$H-NMR (CDCl$_3$, 200 MHz) δ ppm): 7.3 (5H, m), 6.6 (1H, broad s), 5.4 (1H, broad s), 4.2–3.9 (5H, m), 3.5 (3H, s), 1.8–1.7 (3H, m), 1.4 (9H, s), 1.3–1.2 (6H, m)

$^{13}$C-NMR (CDCl$_3$, 50 MHz) δ ppm): 174.2, 172.2, 171.3, 155.3, 134.8, 129.2, 128.7, 127.0, 80.3, 62.4, 61.2, 52.4, 43.6, 37.8, 28.9, 28.1, 26.5, 23.1, 14.0 b) (2SR,1'SR,2'SR,3'RS)-2-(3'-benzylcarbonylaminomethyl-2'-carboxycyclopropyl) glycine To a solution of ethyl (2SR,1'SR,2'SR,3'RS)-N-(tert-butoxycarbonyl)-2-[2'-(ethoxycarbonyl)-3'-(benzylcarbonyl-aminomethyl)cyclopropyl]glycinate (221 mg, 0.48 mmol) in tetrahydrofuran (5 mL), a 2.5M solution of LiOH.H$_2$O (806 mg, 19.2 mmol) in H$_2$O (7.7 mL) was added and the mixture was stirred at room temperature overnight. The following day ethyl acetate (3 mL) was added, the organic layer was separated and the aqueous layer was washed with ethyl acetate (3×3 mL). The aqueous layer was acidified to pH 1 with 1N HCl and extracted into ethyl acetate (5×10 mL). The combined organic layers were dried over magnesium sulfate, filtered and concentrated under vacuum. The residue was dissolved in a 1N solution of HCl in ethyl acetate (2.2 mL, 2.2 mmol) and the solution was stirred overnight at room temperature. It was concentrated under vacuum and the solid was washed with diethyl ether to give the corresponding hydrochloride salt of the title compound. After purification by ion exchange chromatography, 47 mg (33% yield) of (2SR,1'SR,2'SR,3'RS)-2-(3'-benzylcarbonylaminomethyl-2'-carboxycyclopropyl)glycine were obtained as a white solid.

$^{13}$C-NMR (CD$_3$OD, 50 MHz) δ ppm):177.0, 173.9, 172.4, 135.0, 128.8, 128.7, 127.0, 53.8, 42.5, 37.9, 26.6, 26.0, 24.9

Example 20

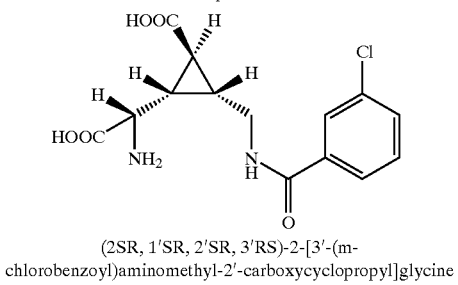

(2SR, 1'SR, 2'SR, 3'RS)-2-[3'-(m-chlorobenzoyl)aminomethyl-2'-carboxycyclopropyl]glycine a) Ethyl (2SR,1'SR,2'SR,3'RS)-N-(tert-butoxycarbonyl)-2-[2'-(ethoxycarbonyl)-3'-(m-chlorobenzoylaminomethyl)cyclopropyl]glycinate To a solution of ethyl (2SR,1'SR,2'SR,3'RS)-N-(tert-butoxycarbonyl)-2-[2'-(ethoxycarbonyl)-3'-(azidomethyl) cyclopropyl]glycinate (100 mg, 0.27 mmol) in ethylacetate (4 mL), platinum (IV) oxide (12 mg, 0.054 mmol) was added and the mixture was allowed to react at room temperature under hydrogen atmosphere for 4 hours. Then, m-chlorobenzoyl chloride (0.069 mL, 0.54 mmol) was added and reaction stirred at room temperature under nitrogen atmosphere overnight. The following day, the mixture was filtered through celite and concentrated under vacuum. The residue was purified by column chromatography using hexane and ethyl acetate 7:3 as eluent to afford 51 mg (39% yield) of ethyl (2SR,1'SR,2'SR,3'RS)-N-(tert-butoxycarbonyl)-2-[2'-(ethoxycarbonyl)-3-(m-chlorobenzoylaminomethyl)-cyclopropyl]glycinate.

$^1$H-NMR (CDCl$_3$, 200 MHz) δ ppm): 7.9 (1H, t, J=1,6 Hz), 7.8–7.7 (2H, dt, J=1,4 Hz, 7,3 Hz), 7.4–7.3 (2H, m), 5.6 (1H, d, J=7,6 Hz), 4.3–4.1 Hz (5H m), 3.1 (2H, ddd, J=3 Hz, 9,9 Hz, 14,6 Hz), 1.9–1.7 (3H, m), 1.4 (9H, s), 1.3–1.2 (6H, m)

$^{13}$C-NMR (CDCl$_3$, 50 MHz) δ ppm): 171.9, 165.5, 155.5, 136.0, 134.4, 131.2, 129.8, 127.4, 125.1, 80.3, 62.2, 60.9, 52.6, 38.2, 28.7, 28.1, 26.4, 23.2, 14.0, 13.9 b) (2SR,1'SR,2'SR,3'RS)-2-[3'-(m-chlorobenzoylaminomethyl-2'-carboxycyclopropyl] glycine To a solution of ethyl (2SR,1'SR,2'SR,3'RS)-N-(tert-butoxycarbonyl)-2-[2'-(ethoxycarbonyl)-3-(m-chlorobenzoylaminomethyl)cyclopropyl]glycinate (302 mg, 0.63 mmol) in tetrahydrofuran (6.5 mL), a 2.5M solution of LiOH.H$_2$O (1.05 g, 25.0 mmol) in H$_2$O (10 mL) was added and the mixture was stirred at room temperature overnight. The following day ethyl acetate (10 mL) was added, organic layer separated and aqueous layer washed with ethyl acetate (3×5 mL). The aqueous layer was acidified to pH 1 with 1N HCl and extracted with ethyl acetate (5×20 mL). The combined organic layers were dried over magnesium sulfate, filtered and concentrated under vacuum. The residue was dissolved in a 1N solution of HCl in ethyl acetate (3.5 mL, 3.5 mmol) and the solution was stirred overnight at room temperature. It was concentrated under vacuum and the solid was washed with diethyl ether to give the corresponding hydrochloride salt of the title compound. After purification by ion exchange chromatography, 97 mg (47% yield) of (2SR,1'SR,2'SR, 3'RS)-2-[3-(m-chlorobenzoylaminomethyl)-2'-carboxycyclopropyl]glycine were obtained as a white solid.

$^{13}$C-NMR (CD$_3$OD, 50 MHz) δ ppm): 175.1, 170.6, 168.5, 137.3, 135.6, 132.7, 131.3, 128.5, 126.7, 53.2, 39.4, 28.1, 27.4, 25.3.

Example 21

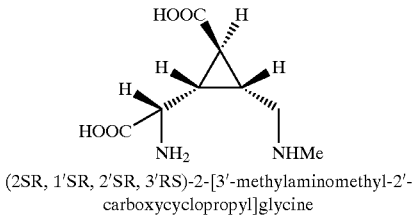

(2SR, 1'SR, 2'SR, 3'RS)-2-[3'-methylaminomethyl-2'-carboxycyclopropyl]glycine a) Ethyl (2SR,1'SR,2'SR,3'RS)-N-(tert-butoxycarbonyl)-2-[2'-(ethoxycarbonyl)-3'-(methylaminomethyl)cyclopropyl]-glycinate To a solution of ethyl (2SR,1'SR,2'SR,3'RS)-N-(tert-butoxycarbonyl)-2-[2'-(ethoxycarbonyl)-3'-azidomethyl cyclopropyl]glycinate (1.35 mmol, 500 mg) in ethyl acetate (20 mL), platinum (IV) oxide (0.27 mmol, 60 mg) was added and the mixture was allowed to react at room temperature under a hydrogen atmosphere for 4 hours. Then, methyl iodide (2.7 mmol, 0.17 mL) was added and the mixture was allowed to react under nitrogen at room temperature overnight. The following day, the mixture was filtered through celite and concentrated under vacuum. The residue was purified by column chromatography using a 4% mixture of methanol in dichloromethane as eluent to afford 380 mg (79% yield) of ethyl (2SR,1'SR,2'SR,3'RS)-N-(tert-butoxycarbonyl)-2-[2'-(ethoxycarbonyl)-3'-(methylaminomethyl)cyclopropyl]-glycinate.

$^1$H-NMR (CDCl$_3$, 200 MHz) δ ppm): 6.7 (1H, broad s), 5.5 (1H, broad s), 4.2–3.9 (5H, m), 3.4–3.0 (2H, m), 2.7 (3H, s), 2.1–1.8 (3H, m), 1.3 (9H, s), 1.2–1.1 (6H, m)

$^{13}$C-NMR (CDCl$_3$, 50 MHz) δ ppm): 171.8, 171.5, 155.3, 80.3, 62.6, 61.2, 52.7, 39.3, 33.3, 28.9, 28.1, 24.7, 24.1, 14.0 b) (2SR,1'SR,2'SR,3'RS)-2-(3'-methylaminomethyl-2'-carboxycyclopropyl)glycine

A solution of ethyl (2SR,1'SR,2'SR,3'RS)-N-(tert-butoxycarbonyl)-2-[2 1-(ethoxycarbonyl)-3'-(methylaminomethyl)cyclopropyl]glycinate (188 mg, 0.52 mmol) in 2N HCl (5 mL) was stirred at room temperature for 5 days. Then, the solvent was evaporated under reduced pressure and the residue was dissolved in 6N HCl (2 mL) and allowed to react at room temperature for 2 days and at 55° C. for 6 hours. The solvent was then removed under vacuum to afford the corresponding hydrochloride salt of the title compound. After purification by ion exchange chromatography, 38 mg (33% yield) of (2SR,1'SR,2'SR, 3'RS)-2-[3'-methylaminomethyl-2'-carboxycyclopropyl] glycine were obtained as a white solid.

$^{13}$C-NMR (D$_2$O/py-d$_5$, 50 MHz) δ ppm): 178.5, 172.9, 53.8, 38.3, 31.9, 27.0, 25.7, 21.9.

Example 22

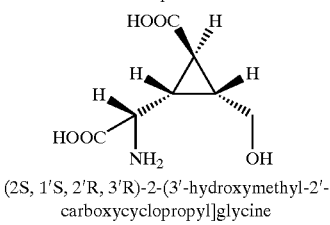

(2S, 1'S, 2'R, 3'R)-2-(3'-hydroxymethyl-2'-carboxycyclopropyl]glycine a) Ethyl (2S,1'S,2'R,3'R)-N-(tert-butoxycarbonyl)-2-[2'-(ethoxycarbonyl)-3'-hydroxymethylcyclopropyl] glycinate The corresponding enantiomers of ethyl (2SR,1'SR, 2'RS, 3'RS)-N-(tert-butoxycarbonyl)-2-[2'-(ethoxycarbonyl)-3'-hydroxymethyl-cyclopropyl]glycinate were separated by chiral HPLC using the following analytical method:
Chiralpak AD 4.6×250 mm
Eluent: 10% MeOH, 10% IPA in Heptane
Flow: 1.0 mL/min.
UV: 220 nm
Isomer #1 retention time=5.5 min
Isomer #2 retention time=7.0 min
Isomer #2, that was identified as the desired enantiomer, was further purified by silica gel chromatography using EtOAc/hexane (1:1) as the eluent to afford 10.21 g of ethyl (2S,1'S,2'R,3'R)-N-(tert-butoxycarbonyl)-2-[2'-(ethoxycarbonyl)-3'-hydroxymethylcyclopropyl] glycinate b) (2S,1'S,2'R,3'R)-2-(3'-hydroxymethyl-2'-carboxycyclopropyl)glycine To a stirred solution of ethyl (2S,1'S,2'R,3'R)-N-(tert-butoxycarbonyl)-2-[2'-(ethoxycarbonyl)-3'-hydroxymethyl-cyclopropyl]glycinate (10.21 g, 29.56 mmol, isomer #2 of the separation above) in CH$_2$Cl$_2$ (50 mL) at 2° C. was added trifluoroacetic acid (22.8 mL, 296 mmol) over a few minutes, maintaining the temperature below 5° C. The mixture was allowed to warm to room temperature and stirred for 2.5 hours. Then, mixture was evaporated under reduced pressure to give a faint yellow oil. The oil was dissolved in CH$_2$Cl$_2$ (35 mL) and the volatiles evaporated (3×). This process was repeated using ethanol (3×40 mL) to afford a faint yellow oil (15.6 g) which was dissolved in 3 N NaOH (49.3 mL, 148 mmol) using a water bath to maintain the temperature slightly above ambient temperature. The faint yellow homogeneous mixture was stirred for 1.25 h before the pH was slowly lowered to 3.5 using concentrated HCl. Once crystallization initiated, the pH was adjusted to 2.55 over 10 min using concentrated HCl. The suspension was cooled to 2° C. and stirred for 2.25 hours before the white solid was collected and washed with cold water (1×12 mL, 2×5 mL). The material was dried in vacuo for several hours at 38° C. and for 2.5 days at room temperature, affording 4.88 g (87% yield) of (2S, 1'S,2'R, 3'R)-2-(3'-hydroxymethyl-2'-carboxycyclopropyl)glycine.

$[α]^{20}_D$=+3.3 (c 1.1, 1 N NaOH)

Example 23

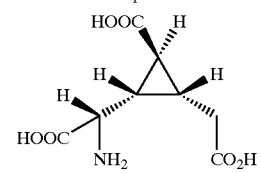

(2SR, 1'SR, 2'RS, 3'RS)-2-(3'-carboxymethyl-2'-carboxycyclopropyl)glycine a) Ethyl (1SR,2SR,6RS,7SR) 3-(tert-butoxycarbonyl)-4-oxo-3-aza-bicyclo[4.1.0]heptane-2,7-dicarboxylate To solution of (2SR,1'SR,2'SR,3'RS) N-(tert-butoxycarbonyl)-2-[2'-(ethoxycarbonyl)-3'-(2'-hydroxyethyl)cyclopropyl]glycinate (1.45 g, 4.48 mmol) in 50 mL of anhydrous CH$_2$Cl$_2$, 8.4 g (22.4 mmol) of PDC (pyridinium dichromate) were added and stirred at room temperature for 2 days. Then, 50 mL of CH$_2$Cl$_2$ were added, the crude was then filtered through celite, and concentrated in vacuo. The residue was purified by column chromatography using ethyl acetate/hexane 1:1 as eluent to afford 0.48 g (34% yield) of ethyl (1SR,2SR,6RS,7SR) 3-(tert-butoxycarbonyl)-4-oxo-3-aza-bicyclo[4.1.0]heptane-2,7-dicarboxylate as a yellow oil.

$^1$H-NMR (300 MHz, CDCl$_3$): 1.25 (t, J=7.1 Hz, 3H) 1.30 (t, J=7.1 Hz, 3H), 1.49 (s, 9H), 1.73 (t, J=4.1 Hz, 1H), 1.95–1.99 (m, 1H), 2.19–2.25 (m, 1H), 2.61 ((dd, J$_1$=18.0 Hz, J$_2$=3.2 Hz, 1H), 2.91 ((dd, J$_1$=18.0 Hz, J$_2$=6.6 Hz, 1H), 4.13 (q, J=7.1 Hz, 2H), 4.25 (m, 2H), 5.05 (d, J=6.9 Hz, 1H) ppm.

$^{13}$C-NMR (75 MHz, CDCl$_3$): 14.0, 14.1, 19.2, 21.3, 24.0, 27.7, 33.2, 56.7, 61.0, 61.8, 84.2, 151.6, 167.7, 169.6, 177.2 ppm.

b) (2SR,1'SR,2'SR,3'RS) 2-[2'-carboxy-(3'-carboxymethyl)cyclopropyl]glycine hydrochloride Ethyl (1SR,2SR,6RS,7SR) 3-(tert-butoxycarbonyl)-4-oxo-3-aza-bicyclo[4.1.0]heptane-2,7-dicarboxylate in 6N HCl (4 mL) was refluxed overnight. The following day, solvent was removed under vacuo to dryness to afford the corresponding hydrochloride of (2SR,1'SR,2'SR,3'RS)2-[2'-carboxy-(3'-carboxymethyl)cyclopropyl]glycine.

¹H-NMR (200 MHz, methanol-d₄): 1.61–1.99 (m, 5H), 3.83 (d, 1H)ppm.

¹³C-NMR (50 MHz, methanol-d₄): 22.5, 24.5, 25.4, 31.9, 51.6, 168.8, 172.4, 173.7 ppm.

Example 24

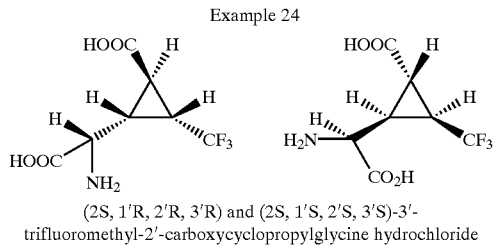

(2S, 1'R, 2'R, 3'R) and (2S, 1'S, 2'S, 3'S)-3'-trifluoromethyl-2'-carboxycyclopropylglycine hydrochloride a) trans-4,4,4-Trifluoro-2-buten-1-yl acetoacetate To a refluxing solution of 4,4,4-trifluoro-2-buten-1-ol (10 g, 79 mmol) and sodium acetate (0.51 g, 6.2 mmol) in anhydrous tetrahydrofuran (27 mL) under nitrogen, a solution of diketene (6.7 mL, 43.1 mmol) in anhydrous tetrahydrofuran (14 mL) was added dropwise over a period of 1 hour. The reaction mixture was heated at reflux for an additional 30 min upon completion of the addition. Then, the reaction mixture mixture was cooled to room temperature and diluted with diethyl ether (100 mL). The resulting solution was washed with a saturated aqueous sodium chloride solution (2×20 mL) and the organic layer was dried over sodium sulfate, filtered and the solvent removed under reduced pressure. The brown residue was purified by column chromatography using a mixture 4:1 of hexane and ethyl acetate as eluent to afford 14.0 g (84% yield) of trans-4,4,4-trifluoro-2-buten-1-yl acetoacetate as a colorless liquid.

¹H-NMR (200 MHz, CDCl₃): 2.25 (s, 3H), 3.51 (s, 2H), 4.78–4.71 (m, 2H), 5.97–5.82 (m, 1H), 6.46–6.33 (m, 1H) ppm.

¹³C-NMR (50 MHz, CDCl₃): 30.2, 50.0, 62.1, 115.0, 119.2, 119.9, 120.4, 120.6, 121.2, 125.7, 131.1, 133.8, 134.0, 134.1, 134.2, 166.7, and 200.5 ppm.

b) trans-4,4,4-trifluoro-2-buten-1-yl diazoacetate

To a solution of trans-4,4,4-trifluoro-2-buten-1-yl acetoacetate (13.7 g, 65.1 mmol) and triethylamine (11.7 mL, 84 mmol) in anhydrous acetonitrile (60 mL), a solution of p-acetamidobenzenesulfonyl azide (20.1 g, 84 mmol) in anhydrous acetonitrile (60 mL) was added dropwise over a period of 30 minutes. A white precipitate was observed after 15–20 minutes and additional acetonitrile (100 mL) was added to facilitate stirring. The resulting mixture was stirred at room temperature for one additional hour. Then, a solution of lithium hydroxyde (9.0 g, 214 mmol) in water (75 mL) was added to the reaction mixture. After stirring for one hour, the resulting mixture was poured onto 2:1 diethyl-ether:ethyl acetate (150 mL) and layers were separated. Aqueous layer was extracted with 2:1 diethylether:ethyl acetate (150 mL) and the combined organic phases were washed with a saturated aqueous sodium chloride solution (50 mL). The resulting organic solution was dried over sodium sulfate, filtered and the solvent removed under reduced pressure. The residue was purified by column chromatography using a mixture 4:1 of hexane and ethyl acetate as eluent to afford 9.4 g (75% yield) of trans-4,4,4-trifluoro-2-buten-1-yl diazoacetate as a yellow oil.

¹H-NMR (200 MHz, CDCl₃): 4.79–4.75 (m, 2H), 4.81 (s, 1H), 5.90–5.75 (m, 1H), 6.48–6.36 (m, 1H) ppm.

¹³C-NMR (50 MHz, CDCl₃): 46.6, 62.3, 115.0, 119.2, 119.9, 120.3, 120.6, 121.3, 125.7, 131.0 134.3, 134.4, 134.5, 134.6, 166.3 ppm.

c) (1RS,5SR,6RS)-6,6,6-trifluoromethyl-3-oxabicyclo[3.1.0]hexan-2-one

To a solution of Cu(TBS)₂ (1.0 g, 2.4 mmol) in anhydrous toluene (750 mL) heated at reflux, a solution of trans-4,4,4-trifluoro-2-buten-1-yl diazoacetate (9.4 g, 48.4 mmol) in anhydrous toluene (750 mL) was added dropwise over a period of 30 hours. After the addition was complete, mixture was allowed to react under reflux for one hour and then cooled to room temperature. The solvent was removed under reduced pressure and the residue was purified by column chromatography using hexane and ethyl acetate 4:1 as eluent. 4.8 g (60% yield) of (1RS,5SR, 6RS)-6,6,6-trifluoromethyl-3-oxabicyclo[3.1.0]hexan-2-one was obtained as a yellow oil.

¹H-NMR (200 MHz, CDCl₃): 1.95–1.87 (m, 1H), 2.44–2.40 (m, 1H), 2.62–2.54 (m, 1H), 4.43–4.37 (m, 2H) ppm.

¹³C-NMR (50 MHz, CDCl₃): 20.1, 20.2, 20.3, 23.6, 24.3, 25.1, 25.8, 68.2, 115.4, 120.8, 126.2, 131.6, 172.3 ppm.

d) Methyl (1RS,2SR,3RS)-2-hydroxymethyl-3-trifluoromethylcyclopropane-1-carboxylate To a solution of (1RS,5SR,6RS)-6,6,6-trifluoromethyl-3-oxabicyclo[3.1.0]hexan-2-one (4.7 g, 28.5 mmol) in tetrahydrofurane (40 mL) at room temperature, a solution of lithium hydroxyde (3.5 g, 83.4 mmol) in water (83 mL) was added. The reaction mixture was stirred overnight at room temperature and the following day the organic phase was removed under vacuo. The resulting aqueous layer was washed with diethyl ether (2×25 mL) and then cooled to 0° C. After the pH was adjusted to 2–3 by addition of 1N HCl, the aqueous layer was extracted with ethyl acetate (6×100 mL). The combined organic phases were dried over sodium sulfate, filtered and the solvent removed under reduced pressure. The resulting carboxylic acid was taken into diethyl ether (100 mL) and cooled to 0° C. and a solution of diazomethane in diethyl ether was added in small portions until TLC showed no starting material remained. The solvent was then removed under reduced pressure to afford the corresponding methyl (1RS,2SR,3RS)-2-hydroxymethyl-3-trifluoromethylcyclopropane-1-carboxylate (5.0 g). This crude was used in the next step without further purification.

¹H-NMR (200 MHz, CDCl₃): 2.01–1.87 (m, 1H), 2.34–2.14 (m, 3H), 3.75(s,3H), 3.80–3.74 (m, 1H), 3.94–3.89 (m, 1H) ppm.

¹³C-NMR (50 MHz, CDCl₃): 20.9, 24.2, 25.0, 25.2, 25.7, 26.5, 52.4, 58.2, 116.4, 121.8, 127.2, 132.6, 170.6 ppm.

e) Methyl (1RS,2SR,3RS)-2-formyl-3-trifluoromethylcyclopropane-1-carboxylate

To a solution of unpurified methyl (1RS,2SR,3RS)-2-hydroxymethyl-3-trifluoromethylcyclopropane-1-carboxylate (5.0 g, 25.2 mmol) in anhydrous dichloromethane (250 mL) at room temperature under nitrogen atmosphere, molecular sieves (4A) (3.8 g) was added. After stirring for 15 min, mixture was cooled to 0° C. and a solution of N-methylmorholine-N-oxide (4.42 g, 37.8 mmol) was added. After 10 min, tetrapropylammonium perruthenate (440 mg, 1.26 mmol) was added in small portions and the mixture was allowed to react at room temperature. The following day, the solvent was removed under vacuo and the residue was taken into ethyl acetate (200 mL). The resulting suspension was filtered through a plug of celite and organic layer was removed to dryness. After purification of the crude by column chromatography using ethyl acetate and hexane 1:4 as eluent, 2.1 g (37% yield) of methyl (1RS,2SR,3RS)-2-formyl-3-trifluoromethylcyclopropropane-1-carboxylate were obtained.

$^1$H-NMR (200 MHz, CDCl$_3$): 2.38–2.45 (m, 1H), 2.51–2.59 (m, 1H), 2.94–3.03, (m, 1H), 3.76 (s, 3H), 9.40 (d, J=5.1 Hz, 1H) ppm.

$^{13}$C-NMR (50 MHz, CDCl$_3$): 24.4, 25.2, 26.0, 26.7, 27.5, 30.8, 52.9, 120.7, 126.2, 131.6, 167.9, 194.5 ppm.

f) Methyl (1RS,2RS,3RS)-2-formyl-3-trifluoromethylcyclopropropane-1-carboxylate

A solution of sodium hydroxide (10.0 g, 250 mmol) in water (100 mL) was added to a solution of methyl (1RS,2SR,3RS)-2-formyl-3-trifluoromethylcyclopropropane-1-carboxylate (1.72 g, 8.8 mmol) in methanol (130 mL), and the mixture was stirred at room temperature for 4 days. Methanol was then removed under reduced pressure and the resulting aqueous layer was washed with diethyl ether (2×25 mL) and cooled to 0° C. After the pH was adjusted to 3–4 by addition of an aqueous solution of citric acid (10–25%), the aqueous layer was extracted with ethyl acetate (6×100 mL). The combined organic phases were dried over sodium sulfate, filtered and the solvent was removed under reduced pressure. The resulting carboxylic acid was taken into diethyl ether (100 mL) and cooled to 0° C., and a solution of diazomethane in diethyl ether was added in small portions until TLC showed no starting material remained. The solvent was removed under reduced pressure and residue purified by column chromatography using hexane and ethyl acetate 4:1 as eluent to afford 1.25 g (73% yield) of an inseparable 1:1 mixture of the corresponding methyl (1RS, 2RS,3RS)-2-formyl-3-trifluoromethylcyclopropropane-1-carboxylate and starting material. This mixture was used in the next step without any other further purification.

$^1$H-NMR (200 MHz, CDCl$_3$): 2.62–2.51 (m, 1H), 2.89–2.83, (t, 1H), 3.77 (s, 3H), 9.28–9.24 (m, 1H) ppm.

g) (2S,1"R,1'R,2'R,3'R) and (2S,1"R,1'S,2'S, 3'S)-N-[(2"-hydroxy-1"-phenyl)ethyl]2-(2'-methoxycarbonyl-3'-trifluoromethylcyclopropyl) glycinonitrile To a solution of a 1:1 mixture of methyl (1RS,2RS,3RS)-2-formyl-3-trifluoromethylcyclopropropane-1-carboxylate and methyl (1RS,2SR,3RS)-2-formyl-3-trifluoromethyl cyclopropropane-1-carboxylate (1.25 g, 6.3 mmol) in methanol (63 mL), (R)-(−)-2-phenylglycinol (0.96 g, 7.0 mmol) was added. The mixture was stirred at room temperature for two hours and then cooled to 0° C. Trimethylsilylcyanide (1.66 mL, 12.4 mmol) was added to the mixture and allowed to react at room temperature overnight. The following day the solvent was removed under reduced pressure and residue was purified by column chromatography using ethyl acetate and hexane 1:3 as eluent to afford 1.59 g (73% yield) of a mixture of four aminonitriles. (2S,1"R,1'R,2'R,3'R) and (2S,1"R, 1'S,2'S,3'S)-N-[(2"-hydroxy-1"-phenyl)ethyl]-2-(2'-methoxycarbonyl-3'-trifluoromethyl cyclopropyl) glycinonitrile (glycinonitriles A and B) were purified and separated by column chromatography using dichloromethane and acetone 18:1 as eluent.

Glycinonitrile A
$^1$H-NMR (200 MHz, acetone-d$_6$): 2.02 (m, 1H), 2.27 (m, 1H), 2.40 (t, 1H), 3.06 (d, 1H), 3.60–3.66 (m, 2H), 3.69 (s, 3H), 3.99 (t, 1H), 4.05–4.08 (m, 2H), 7.26–7.45 (m, 5H)ppm.

$^{13}$C-NMR (50 MHz, CDCl$_3$): 22.1, 25.4, 26.2, 26.9, 27.7, 47.4, 52.7, 63.1, 66.6, 118.1, 121.8, 127.3, 128.3, 128.7, 139.2, 169.7 ppm.

Glycinonitrile B
$^1$H-NMR (200 MHz, CDCl$_3$): 2.09 (t, 1H), 2.15 (m, 1H), 2.32 (m, 1H), 2.59 (bs, 1H), 3.24 (d, 1H), 3.74 (s, 3H), 3.79–3.95 (m, 2H), 4.09 (dd, 2H), 7.28–7.34 (m, 5H) ppm.

$^{13}$C-NMR (50 MHz, CDCl$_3$): 21.4, 21.5, 25.4, 26.1, 26.9, 27.0, 46.0, 52.7, 63.0, 66.9, 117.9, 121.5, 126.9, 127.7, 128.4, 128.6, 132.3, 136.9, 169.9 ppm.

h) (2S,1'R,2'R,3'R) and (2S,1'S,2'S,3'S)-3'-trifluoromethyl-2'-carboxycyclopropylglycine hydrochloride Lead tetraacetate (35.7 mg, 0.08 mmol) was added to a solution of the glycinonitrile B of step g) (25.1 mg, 0.073 mmol) in a 1:1 mixture of methanol and dichloromethane (0.6 mL) at 0° C. After 10 minutes, water (0.3 mL) was added and mixture filtered off through celite. The solvent was removed under reduced pressure and residue was taken into 4N HCl (4 mL) and refluxed overnight. The following day, the solvent was removed under vacuo to dryness to afford the corresponding hydrochloride salt (Aminoacid B).

Aminoacid B
$^1$H-NMR (200 MHz, methanol-d$_4$): 3.83 (d, J=14 Hz, 1H), 2.56–2.49 (m, 2H), 2.08–2.02 (m, 1H) ppm.

$^{13}$C-NMR (50 MHz, methanol-d4): 22.7, 24.1, 25.4, 25.7, 26.0, 26.3, 63.3, 121.9, 124.1, 126.3, 129.2, 168.8, 171.0 ppm.

Example 25

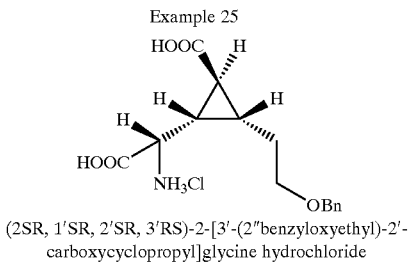

(2SR, 1'SR, 2'SR, 3'RS)-2-[3'-(2"benzyloxyethyl)-2'-carboxycyclopropyl]glycine hydrochloride a) Ethyl (2SR,1'SR,2'SR,3'RS)-N-(tert-butoxycarbonyl)-2-[2'-(ethoxycarbonyl)-3'-(2"-benzyloxyethyl) cyclopropyl]glycinate To a mixture of ethyl (2SR,1'SR,2'SR,3'RS)-N-(tert-butoxycarbonyl)-2-[2'-(ethoxycarbonyl)-3'-(2"-hydroxyethyl)cyclopropyl]glycinate (0.84 mmol, 300 mg) and benzyl 2, 2, 2,-trichloroacetimidate (1.01 mmol, 0.19 mL) in a 2:1 mixture of cyclohexane and dichloromethane (18 mL) at room temperature under nitrogen atmosphere, trifluoromethanesulfonic acid (catalytic amount) was added. The mixture was allowed to react at room temperature for two days and then quenched with water (5 mL). The aqueous phase was extracted with dichloromethane (2×5 mL) and the combined organic layers was dried over magnesium sulfate and evaporated in vacuo. The resulting residue was purified by column chromatography using a hexane and ethyl acetate 9:1 as eluent to afford 193 mg (51% yield) of ethyl (2SR, 1'SR,2'SR,3'RS)-N-(tert-butoxycarbonyl)-2-[2'-(ethoxycarbonyl)-3'-(2"-benzyloxyethyl)cyclopropyl] glycinate.

¹H-NMR (CDCl₃, 200 MHz) δ(ppm): 7.3–7.2, (5H, m), 5.3 (1H, broad s), 4.5 (2H, s), 4.3–4.0 (5H, m), 3.6–3.5 (2H, m), 2.1 (1H, m), 2.0–1.7 (5H, m), 1.4 (9H, s), 1.2–1.1 (6H)

¹³C-NMR (CDCl₃, 200 MHz) δ(ppm): 173.2, 171.3, 157.6, 138.2, 128.3, 127.5, 80.1, 72.9, 69.4, 61.6, 60.7, 52.2, 29.6, 28.2, 27.4, 25.1, 24.7, 14.1 b) (2SR,1'SR,2'SR,3'RS)-2-[3'-(2"-benzyloxyethyl)-2'-carboxycyclopropyl]glycine hydrochloride To a solution of ethyl (2SR,1'SR,2'SR,3'RS)-N-(tert-butoxycarbonyl)-2-[2'-(ethoxycarbonyl)-3'-(2"-benzyloxyethyl)cyclopropyl]glycinate (174 mg, 0.39 mmol) in tetrahydrofuran (4 mL), a 2.5M solution of LiOH.H₂O in H₂O (6.2 mL, 15.5 mmol) was added and the mixture was stirred at room temperature overnight. The following day, diethyl ether was added, and organic layer was separated. The aqueous layer was washed with diethylether (3×3 mL). The aqueous layer was acidified to pH 1 with 1N HCl and extracted in diethyl ether (5×5 mL). The combined organic layers were dried over magnesium sulfate, filtered and concentrated under vacuum. The residue was dissolved in a 1N solution of HCl in ethyl acetate (8 mL, 80 mmol) and the solution was stirred overnight at room temperature. It was concentrated under vacuum and the solid was washed with Et₂O to give 25 mg (19% yield) of the title compound.

¹³C-NMR (CDCl₃, 200 MHz) δ(ppm): 174.9, 169.6, 137.7, 128.1, 127.5, 72.5, 68.8, 51.8, 27.6, 26.0, 25.1, 24.7

Example 26

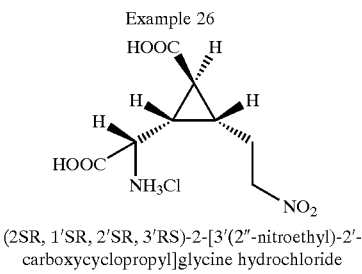

(2SR, 1'SR, 2'SR, 3'RS)-2-[3'(2"-nitroethyl)-2'-carboxycyclopropyl]glycine hydrochloride a) Ethyl (2SR,1'SR,2'SR,3'RS)-N-(tert-butoxycarbonyl)-2-[2'-(ethoxycarbonyl)-3'-(2"-diphenylphosphoryloxyethyl)cyclopropyl]glycinate To a solution of ethyl (2SR,1'SR,2'SR,3'RS)-N-(tert-butoxycarbonyl)-2-[2'-(ethoxycarbonyl)-3'-(2"-hydroxyethyl)cyclopropyl]glycinate (100 mg, 0.28 mmol) in anhydrous toluene (2 mL) at room temperature under nitrogen atmosphere, diphenylphosphorylazide (0.053 mL, 0.33 mmol) was added. After 30 minutes, DBU was added (0.046 mL, 0.31 mmol) and the reaction mixture stirred overnight. The following day reaction mixture was quenched with water (2 mL) and aqueous phase extracted with ethyl acetate (2×2 mL). The combined organic layers were dried over magnesium sulfate, filtrated and evaporated under reduced pressure. The resulting residue was purified by column chromatography using hexane and ethyl acetate 7:3 as eluent to afford 132 mg (80% yield) of ethyl (2SR, 1'SR,2'SR, 3'RS)-N-(tert-butoxycarbonyl)-2-[2'-(ethoxycarbonyl)-3'-(2"-diphenylphosphoryloxyethyl)cyclopropyl]glycinate ¹H-NMR (CDCl₃, 200 MHz) δ(ppm): 7.4–7.2 (1OH, m), 5.2 (1H, broad s), 4.3 (2H, q, J=7 Hz), 4.2 (2H, q, J=7.2 Hz), 4.0 (2 H, dd, J=1,8 Hz, 7 Hz), 2.3–2.1 (1H, m), 1.8–1.6 (4H, m), 1.4 (9H, s), 1.2 (3H, t, J=7,2 Hz), 1.1 (3H, t, J=7,2 Hz)

¹³C-NMR (CDCl₃, 200 MHz) δ(ppm): 173.9, 172.4, 151.4, 129.7, 125.2, 120.0, 119.9, 80.7, 68.2, 61.7, 60.7, 52.1, 29.5, 28.8, 28.1, 24.5, 23.7, 14.0 b) Ethyl (2SR,1'SR,2'SR,3'RS)-N-(tert-butoxycarbonyl)-2-[2'-(ethoxycarbonyl)-3'-(2"-azidoethyl)cyclopropyl]glycinate A solution of ethyl (2SR,1'SR,2'SR,3'RS)-N-(tert-butoxycarbonyl)-2-[2'-(ethoxycarbonyl)-3'-(2"-diphenylphosphoryloxyethyl)cyclopropyl]glycinate (445 mg, 0.75 mmol) and sodium azide (98 mg, 1.5 mmol) in anhydrous dimethylformamide (7 mL) was stirred at room temperature for two days and then heated at 60° overnight. Then, the reaction was quenched with water (10 mL) and the aqueous phase was extracted with ethyl acetate (3×5 mL). The combined organic layers were washed with water (6×5 mL). The organic layer was dried over magnesium sulfate and the solvent evaporated in vacuo. The resulting residue was purified by column cromatography using hexane and ethyl acetate 8:2 as eluent to afford 216 mg (75% yield) of ethyl (2SR,1'SR,2'SR,3'RS)-N-(tert-butoxycarbonyl)-2-[2'-(ethoxycarbonyl)-3'-(2"-azidoethyl)cyclopropyl]glycinate.

¹H-NMR (CDCl₃, 200 MHz) δ(ppm): 5.2 (1H, broad s), 4.2 (2H, q, J=7,2 Hz), 4.1 (2H, q, J=7.2 Hz), 3.9 (1H, m), 3.4 (2H, t, J=6, 6 Hz), 2.0 (1H, m), 1.7–1.6 (3H, m), 1.4 (9H, s), 1.3 (3H, t, J=7,2 Hz), 1.2 (3H, t, J=7,2 Hz)

¹³C-NMR (CDCl₃, 200 MHz) δ(ppm): 172.5, 170.9, 153.9,79.9, 61.5, 60.6, 52.0, 50.7, 29.5, 28.0, 27.5, 24.8, 13.9 c) Ethyl (2SR,1'SR,2'SR,3'RS)-N-(tert-butoxycarbonyl)-2-[2'-(ethoxycarbonyl)-3'-(2"-nitroethyl) cyclopropyl]-glycinate To a solution of ethyl (2SR,1'SR,2'SR,3'RS)-N-(tert-butoxycarbonyl)-2-[2'-(ethoxycarbonyl)-3'-(2"-azidoethyl) cyclopropyl]glycinate (167 mg, 0.43 mmol) in ethyl acetate (4 mL), platinum (IV) oxide was added (19.5 mg, 0.086 mmol) and the mixture allowed to react at room temperature under a hydrogen atmosphere for 4 hours. Then, mixture was filtered through celite and concentrated evaporated to dryness. The resulting residue was disolved in dichloromethane (4 mL), cooled to 0° C. and treated in one portion with 80% 3-chloroperoxybenzoic acid (223 mg, 1.29 mmol) and stirred at room temperature overnight. The following day, 2-propanol was added to the reaction mixture and then poured into a 1:1 mixture of a saturated aqueous solution of sodium bicarbonate and ethyl acetate (10 mL). The aqueous layer was extracted with ethyl acetate (3×10 mL), and the combined organic layers washed with brine and dried over sodium sulfate. The solvent was evaporated under vacuo, and the resulting residue was purified by column chromatography using hexane and ethyl acetate 9:1 as eluent to afford 20 mg (12% yield) of ethyl (2SR,1'SR,2'SR,3'RS)-N-(tert-butoxycarbonyl)-2-[2'-(ethoxycarbonyl)-3'-(2"-nitroethyl)-cyclopropyl]glycinate.

¹H-NMR (CDCl₃, 200 MHz) δ(ppm): 4.6 (2H, t, J=6,9 Hz), 4.5–4.0 (5H, m), 2.4–2.0 (1H, m), 1.8–1.6 (4H, m), 1.4 (9H, s), 1.3 (3H, t, J=7,2 Hz), 1.2 (3H, t, J=7,2 Hz)

¹³C-NMR (CDCl₃, 200 MHz) δ(ppm): 170.8, 170.0, 155.2, 80.4, 74.4, 62.0, 61.0, 51.8, 29.8, 28.1, 25.8, 24.3, 23.9, 14.0 d) (2SR,1'SR,2'SR,3'RS)-2-[3'-(2"-nitroethyl)-2'-carboxycyclopropyl]glycine hydrochloride A 2.5M solution of LiOH.H₂O in H₂O (1.5 mL, 3.6 mmol) was added to a solution of ethyl (2SR,1'SR,2'SR, 3'RS)-N-(tert-butoxycarbonyl)-2-[2'-(ethoxycarbonyl)-3'-(2"-nitroethyl)cyclopropyl]glycinate (24.0 mg, 0.06 mmol) in THF (1 mL) and the mixture was stirred at room temperature overnight. Et$_2$O was added (1 mL), the organic layer was separated and the aqueous layer was washed with Et$_2$O (3×1 mL). The aqueous layer was acidified to pH 1 with 1N HCl and extracted in Et$_2$O (5×2 mL). The combined organic layers were dried over MgSO$_4$, filtered and concentrated under vacuum. The residue was dissolved in a 2M solution of HCl in Et$_2$O (4 mL/mmol) and the solution was stirred overnight at room temperature. The mixture was concentrated under vacuum and the solid was washed with Et$_2$O to give 3 mg (16% yield) of the title compound.

$^{13}$C-NMR (CDCl$_3$, 200 MHz) δ(ppm): 173.3, 166.7, 74.1, 51.6, 29.2, 25.3, 24.4, 23.9

Example 27

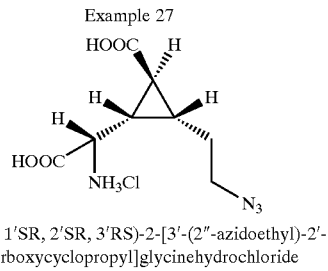

(2SR, 1'SR, 2'SR, 3'RS)-2-[3'-(2''-azidoethyl)-2'-carboxycyclopropyl]glycinehydrochloride a) (2SR,1'SR,2'SR,3'RS)-2-[3'-(2''-azidoethyl)-2'-carboxycyclopropyl]glycine hydrochloride A 2.5M solution of LiOH.H$_2$O in H$_2$O (7.7 mL, 19.2 mL) was added to a solution of ethyl (2SR,1'SR,2'SR,3'RS)-N-(tert-butoxycarbonyl)-2-[2'-(ethoxycarbonyl)-3'-(2''-azidoethyl)cyclopropyl]glycinate (185 mg, 0.48 mmol) in THF (5 mL) and the mixture was stirred at room temperature overnight. Et$_2$O was added (5 mL), the organic layer was separated and the aqueous layer was washed with Et$_2$O (3×5 mL). The aqueous layer was acidified to pH 1 with 1N HCl and extracted in Et$_2$O (5×10 mL). The combined organic layers were dried over MgSO$_4$, filtered and concentrated under vacuum. The residue was dissolved in a 2M solution of HCl in Et$_2$O (4 mL) and the solution was stirred overnight at room temperature. The mixture was concentrated under vacuum and the solid was washed with Et$_2$O to afford 117 mg (90% yield) of the title compound.

$^1$H-NMR (CDCl$_3$, 200 MHz) δ(ppm): 3.81 (1H, d, J=10,4 Hz), 3.4 (2H, t, J=6,9 Hz), 2.1 (1H, m), 1.9–1.5 (5H, m).

$^{13}$C-NMR (CDCl$_3$, 200 MHz) δ(ppm): 173.9, 169.1, 51.7, 50.5, 27.0, 26.0, 25.0, 24.6.

Example 28

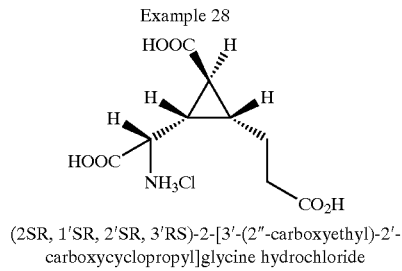

(2SR, 1'SR, 2'SR, 3'RS)-2-[3'-(2''-carboxyethyl)-2'-carboxycyclopropyl]glycine hydrochloride a) Ethyl (2SR,1'SR,2'SR,3'RS)-N-(tert-butoxycarbonyl)-2-[2'-(ethoxycarbonyl)-3'-(2''-p-toluensulfonyloxyethyl)cyclopropyl]glycinate To a solution of ethyl (2SR,1'SR,2'SR,3'RS)-N-(tert-butoxycarbonyl)-2-[2-(ethoxycarbonyl)-3'-(2''-hydroxyethyl)cyclopropyl]glycinate (200 mg, 0.56 mmol) in pyridine (10 mL) two equivalents of p-toluenesulfonyl chloride (0.21 g, 1.11 mmol) were added at room temperature and the reaction was stirred for 40 hours. Then, H$_2$O and EtOAc were added and the organic layer was separated. The aqueous layer was extracted with EtOAc (3×) and the combined organic layers were washed with H$_2$O (5×), dried over MgSO$_4$, filtered and concentrated under vacuum. The residue was purified by column chromatography using a 2:1 mixture of hexane/EtOAc as eluent to afford 110 mg (38% yield) of ethyl (2SR,1'SR,2'SR,3'RS)-N-(tert-butoxycarbonyl)-2-[2'-(ethoxycarbonyl)-3'-(2''-p-toluensulfonyloxyethyl)-cyclopropyl]glycinate.

$^1$H-NMR (CDCl$_3$, 200 MHz) δ(ppm): 7.7 (2H, d, J=8 Hz), 7.2 (2H, d, J=8 Hz), 5.5 (1H, d, J=8 Hz), 4.2–3.7 (7H, m), 2.3 (1H, s), 2.2–1.5 (5H, m), 1.5 (9H, s), 1.3–1.1 (6H, m)

$^{13}$C-NMR (CDCl$_3$, 50 MHz) δ(ppm): 172.4, 170.9, 155.3, 144.7, 132.8, 129.8, 127.8, 80.0, 69.2, 61.7, 60.7, 52.0, 29.5, 28.1, 27.6, 24.4, 23.6, 21.5, 14.0 b) Ethyl (2SR,1'SR,2'SR,3'RS)-N-(tert-butoxycarbonyl)-2-[2'-(ethoxycarbonyl)-3'-(2''-cyanoethyl)cyclopropyl]glycinate To a solution of ethyl (2SR,1'SR,2'SR,3'RS)-N-(tert-butoxycarbonyl)-2-[2'-(ethoxycarbonyl)-3'-(2''-p-toluensulfonyloxyethyl)cyclopropyl]glycinate (500 mg, 0.97 mmol) in DMSO (10 mL) five equivalents of potassium cyanide (0.31 g, 4.85 mmol) were added at room temperature and the reaction was stirred for 5 days. Then, H$_2$O and EtOAc were added and the organic layer separated. The aqueous layer was extracted with EtOAc (3×) and the combined organic layers were washed with H$_2$O (5×), dried over MgSO$_4$, filtered and concentrated under vacuum. The residue was purified by column chromatography using a 2:1 mixture of hexane/EtOAc as eluent to afford 180 mg (50% yield) of ethyl (2SR,1'SR,2'SR,3'RS)-N-(tert-butoxycarbonyl)-2-[2'-(ethoxycarbonyl)-3'-(2''-cyanoethyl)cyclopropyl] glycinate.

$^1$H-NMR (CDCl$_3$, 200 MHz) δ(ppm): 5.3 (1H, d, J=8 Hz), 4.2–3.8 (5H, m), 2.5 (2H, t, J=7 Hz), 2.3–1.5 (5H, m), 1.4 (9H, s), 1.3–1.1 (6H, m)

$^{13}$C-NMR (CDCl$_3$, 50 MHz) δ(ppm): 172.4, 170.9, 155.3, 118.9, 80.2, 61.6, 60.9, 52.0, 29.9, 28.1, 26.1, 24.5, 24.2, 16.9, 14.0 c) (2SR,1'SR,2'SR,3'RS)-2-[3'-(2''-carboxyethyl)-2'-carboxycyclopropyl]glycine hydrochloride (3)

A solution of ethyl (2SR,1'SR,2'SR,3'RS)-N-(tert-butoxycarbonyl)-2-[2'-(ethoxycarbonyl)-3'-(2''-cyanoethyl)cyclopropyl] glycinate (50 mg, 0.14 mmol) in 1N HCl (4 mL) was refluxed overnight. The residue was concentrated under vacuum, washed with EtOAc and dried under vacuum giving rise to 40 mg (68% yield) of the title compound.

$^1$H-NMR (D$_2$O, 200 MHz) δ(ppm): 3.8 (1H, d, J=11 Hz), 2.7–1.5 (7H, m)

$^{13}$C-NMR (D$_2$O/MeOH-d$_4$, 50 MHz) δ(ppm): 178.7, 177.2, 171.5, 53.2, 34.2, 28.5, 27.7, 26.0, 23.9

Example 29

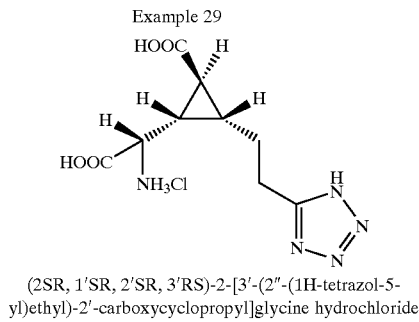

(2SR, 1'SR, 2'SR, 3'RS)-2-[3'-(2"-(1H-tetrazol-5-yl)ethyl)-2'-carboxycyclopropyl]glycine hydrochloride a) (2SR,1'SR,2'SR,3'RS)-2-[3'-(2"-(1H-tetrazol-5-yl)-ethyl)-2'-carboxycyclopropyl]glycine hydrochloride To a solution of ethyl (2SR,1'SR,2'SR,3'RS)-N-(tert-butoxycarbonyl)-2-[2'-(ethoxycarbonyl)-3'-(2"-cyanoethyl)cyclopropyl]glycinate (50 mg, 0.14 mmol) in toluene (0.3 mL), two equivalents of tributyltin azide (0.28 mmol, 92 mg) were added under nitrogen at room temperature and the mixture was heated at 60 C. for 3 days. After cooling down, 1N HCl (4 mL) was added and the resulting reaction mixture was refluxed overnight. After cooling down, EtOAc was added and the organic layer was separated. The aqueous layer was washed with EtOAc (3×) and then concentrated under vacuum. The solid residue was washed with diethyl ether and dried under vacuum giving rise to 36 mg (64% yield) of the title compound.

$^1$H-NMR (D$_2$O/MeOH-d$_4$, 200 MHz) δ(ppm): 3.7 (2H, d, J=11 Hz), 3.0 (2H, m), 2.3–1.4 (5H, m)

$^{13}$C-NMR (D$_2$O/MeOH-d$_4$, 50 MHz) δ(ppm): 176.5, 171.2, 157.3, 53.2, 28.1, 27.4, 26.6, 26.2, 23.4

Example 30

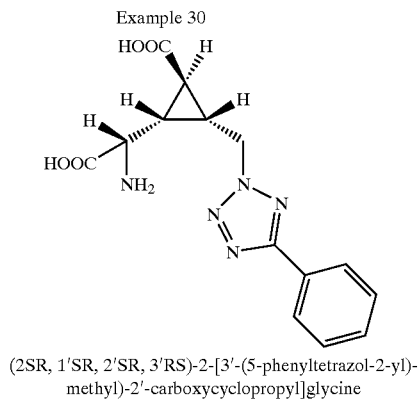

(2SR, 1'SR, 2'SR, 3'RS)-2-[3'-(5-phenyltetrazol-2-yl)-methyl)-2'-carboxycyclopropyl]glycine a) Ethyl (2SR,1'SR,2'SR,3'RS)-N-(tert-butoxycarbonyl)-2-[2'-(ethoxycarbonyl)-3'-(5-phenyltetrazol-2-yl)-methylcyclopropyl]glycinate Diethyl azodicarboxylate (2.16 mmol, 0.34 mL) was added to a solution of triphenylphosphine (2.16 mmol, 0.57 g) in anhydrous THF (40 mL) under nitrogen at room temperature. Then, a solution of ethyl (2SR,1'SR,2'RS,3'RS)-N-( tert-butoxycarbonyl)-2-[2'-(ethoxycarbonyl)-3'-hydroxymethyl-cyclopropyl]glycinate (1.74 mmol, 600 mg) in THF (10 mL) and 5-phenyl-1H-tetrazole (1.13 mmol, 0.15 g) were subsequently added and the reaction mixture stirred for 7 days at room temperature. The reaction mixture was quenched with water, extracted with EtOAc, and the combined organic layers were dried over magnesium sulfate, filtered and concentrated under vacuum. The residue was purified by column chromatography using a 2:1 mixture of hexane/EtOAc as eluent to afford 500 mg (61% yield) of ethyl (2SR,1'SR,2'SR,3'RS)-N-(tert-butoxycarbonyl)-2-[2'-(ethoxycarbonyl)-3'-(5-phenyltetrazol-2-yl)methylcyclopropyl]glycinate.

$^1$H-NMR (CDCl$_3$, 200 MHz) δ(ppm): 8.1 (2H, m), 7.4 (3H, m), 5.6 (1H, d, J=8 Hz), 5.1 (1H, dd, J=6, 14 Hz), 4.7 (1H, dd, J=8,14 Hz), 4.3–3.9 (5H, m), 2.3–1.9 (3H, m), 1.4 (9H, s), 1.2–1.1 (6H, m)

$^{13}$C-NMR (CDCl$_3$, 50 MHz) δ(ppm): 171.5, 170.5, 165.0, 155.3, 130.2, 128.3, 127.3, 126.7, 80.2, 61.7, 60.9, 51.7, 29.4, 28.1, 25.1, 24.3, 13.9 b) (2SR,1'SR,2'SR,3'RS)-2-[3'-(5-phenyl-tetrazol-2-yl)methyl-2'-carboxycyclopropyl]glycine A 2.5M solution of LiOH.H$_2$O in H$_2$O (16.8 mL, 42 mmol) was added to a solution of ethyl (2SR,1'SR,2'SR,3'RS)-N-(tert-butoxycarbonyl)-2-[2'-(ethoxycarbonyl)-3'-(5-phenyltetrazol2-yl)methylcyclopropyl]glycinate (0.5 g, 1.05 mmol) in THF (10 mL) and the mixture was stirred at room temperature overnight. EtOAc was added, the organic layer was separated and the aqueous layer was washed with EtOAc (3×). The aqueous layer was acidified to pH 1 with 1N HCl and extracted in EtOAc (5×). The combined organic layers were dried over MgSO$_4$, filtered and concentrated under vacuum. The residue was dissolved in a 1N solution of HCl in EtOAc (8 mL) and the solution was stirred overnight at room temperature. It was concentrated under vacuum and the solid was washed with Et$_2$O. The final aminoacid was isolated by ion exchange chromatography (150 mg, 50% yield).

$^1$H-NMR (D$_2$O/Py-d$_5$, 200 MHz) δ(ppm): 7.5 (2H, m), 7.0 (3H, m), 5.1 (1H, dd, J=6, 14 Hz), 4.3 (1H, dd, J=10, 14 Hz), 3.5 (1H, d, J=10 Hz), 2.1–1.8 (3H, m)

$^{13}$C-NMR (D$_2$O/Py-d$_5$, 50 MHz) δ(ppm): 178.4, 172.9, 164.5, 130.8, 129.1, 126.7, 126.2, 54.9, 53.2, 28.5, 26.5, 24.5

What is claimed is:

1. A compound of the formula:

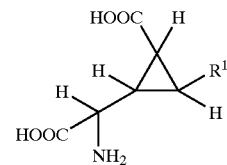

I in which R$^1$ is halo-C$_{1-10}$ alkyl; halo-C$_{2-10}$ alkenyl; or (CH$_2$)$_n$Y in which n is 1 or 2 and Y is OH, CN, N$_3$, SH, S(O)$_p$R$^4$, S(O)$_3$H, NH$_2$, NHR$^5$, NR$^6$R$^7$, NHCOR$^8$, NO$_2$, CO$_2$H, CONHR$^9$, 1H-tetrazol-5-yl, 5-phenyltetrazol-2-yl, or PO$_3$H$_2$; R$^3$, R$^5$, R$^6$, R$^7$, R$^8$ and R$^9$ are each selected independently from C$_{1-4}$ alkyl, aryl and aryl-C$_{1-4}$ alkyl; R$^4$ is selected from C$_{1-4}$ alkyl, aryl, aryl-C$_{1-4}$ alkyl, 1H-tetrazol-5-yl, carboxy-C$_{1-4}$ alkyl and 1H-tetrazol-5-yl-C$_{1-4}$ alkyl; and p is 0, 1, 2 or 3;

or a salt or ester thereof.

2. A compound as claimed in claim 1 of the configuration

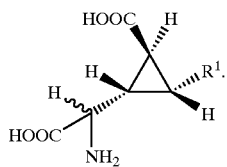

3. A compound as claimed in claim 1 of the configuration

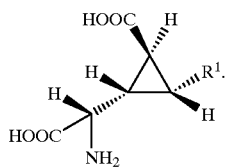

4. A compound according to any one of claims 1 to 3, in which $R^4$ is selected from $C_{1-4}$ alkyl, aryl, aryl-$C_{1-4}$ alkyl, and 1H-tetrazol-5-yl-$C_{1-4}$ alkyl.

5. A compound according to any one of claims 1 to 3, in which $R^1$ is selected from fluoromethyl, trifluoromethyl, 2-fluoroethyl, 2,2,2-trifluoroethyl, chloromethyl, 2-chloroethyl, trichloromethyl, and 2,2,2-trichloroethyl, 2-fluorovinyl, 2,2-difluorovinyl, hydroxymethyl, 2-hydroxyethyl, cyanomethyl, 2-cyanoethyl, azidomethyl, 2-azidoethyl, mercaptomethyl, 2-mercaptoethyl, methanethiomethyl, 2-methanethioethyl, 1H-tetrazol-5-ylthiomethyl, carboxymethylthiomethyl, phenylthiomethyl, methanesulfinylmethyl, 2-methanesulfinylethyl, methanesulfonylmethyl, phenylsulfinylmethyl, phenylsulfonylmethyl, 2-methanesulfonylethyl, 2-phenylthioethyl, 2-benzylthioethyl, aminomethyl, acetylaminomethyl, benzoylaminomethyl, 3-chlorobenzoylaminomethyl, benzylcarbonylaminomethyl, methylaminomethyl, nitromethyl, 2-nitroethyl, 1H-tetrazol-5-ylmethyl, 2-(1H-tetrazol-5-yl)ethyl, 5-phenyltetrazol-2-ylmethyl, carboxymethyl, 2-carboxyethyl, aminocarbonylmethyl, phosphonomethyl, acetamidomethyl, benzamidomethyl, and 2-benzamidoethyl.

6. A compound according to claim 4, in which $R^1$ is selected from fluoromethyl, 2-fluoroethyl, trifluoromethyl, trichloromethyl, trichloroethyl, 2-trichloroethyl, 2-fluorovinyl, 2,2-difluorovinyl, hydroxymethyl, cyanomethyl, 2-cyanoethyl, azidomethyl, 2-azidoethyl, mercaptomethyl, methanethiomethyl, 2-methanethioethyl, 1H-tetrazol-5-ylthiomethyl, methanesulfinylmethyl, 2-methanesulfinylethyl, methanesulfonylmethyl, 2-methanesulfonylethyl, aminomethyl, acetylaminomethyl, nitromethyl, 1H-tetrazol-5-ylmethyl, carboxymethyl, 2-carboxyethyl, methylcarboxamide, phosphonomethyl, acetamidomethyl and benzamidomethyl.

7. A compound according to claim 6, in which $R^1$ is hydroxymethyl.

8. A compound according to claim 1, which is selected from:

(2SR,1'SR,2'RS,3'RS)-2-(3'-hydroxymethyl-2'-carboxycyclopropyl)glycine;
(2SR,1'SR,2'SR,3'RS)-2-[(3'-(2''-hydroxyethyl)-2'-carboxy)cyclopropyl]glycine;
(2SR,1'RS,2'RS,3'RS)-2-[3'-mercaptomethyl-2'-carboxycyclopropyl]glycine;
(2SR,1'RS,2'RS,3'RS)-2-[3'-carboxymethylthiomethyl-2'-carboxycyclopropyl]glycine;
(2SR,1'RS,2'RS,3'RS)-2-[3'-(1H-tetrazol-5-ylthiomethyl)-2'-carboxycyclopropyl]glycine;
(2SR,1'RS,2'RS,3'RS)-2-[(3'-(2''-mercaptoethyl)-2'-carboxy)cyclopropyl]glycine;
(2SR,1'RS,2'RS,3'RS)-2-[3'-methylthiomethyl-2'-carboxycyclopropyl]glycine;
(2SR,1'RS,2'RS,3'RS)-2-[3'-phenylthiomethyl-2'-carboxycyclopropyl]glycine;
(2SR,1'SR,2'SR,3'RS)-2-[(3'-(2''-phenylthioethyl)-2'-carboxycyclopropyl]glycine;
(2SR,1'SR,2'SR,3'RS)-2-[(3'-(2''-benzylthioethyl)-2'-carboxycyclopropyl]glycine;
(2SR,1'RS,2'RS,3'RS)-2-[3'-methylsulfonylmethyl-2'-carboxycyclopropyl]glycine;
(2SR,1'RS,2'RS,3'RS)-2-[3'-phenylsulfonylmethyl-2'-carboxycyclopropyl]glycine;
(2SR,1'SR,2'SR,3'RS)-2-[3'-azidomethyl-2'-carboxycyclopropyl]glycine;
(2SR,1'SR,2'SR,3'RS)-2-[(3'-(2'-fluoroethyl)-2'-carboxycyclopropyl]glycine;
(2SR,1'SR,2'SR,3'RS)-2-[(3'-(2''-chloroethyl)-2'-carboxycyclopropyl]glycine;
(2SR,1'SR,2'SR,3'RS)-2-[3'-acetylaminomethyl-2'-carboxycyclopropyl]glycine;
(2SR,1'SR,2'SR,3'RS)-2-[3'-benzoylaminomethyl-2'-carboxycyclopropyl]glycine;
(2SR,1'SR,2'SR,3'RS)-2-[3'-aminomethyl-2'-carboxycyclopropyl]glycine;
(2SR,1'SR,2'SR,3'RS)-2-[3'-benzylcarbonylaminomethyl-2'-carboxycyclopropyl]glycine;
(2SR,1'SR,2'SR,3'RS)-2-[3'-(m-chlorobenzoyl)aminomethyl-2'-carboxycyclopropyl]glycine;
(2SR,1'SR,2'SR,3'RS)-2-[3'-methylaminomethyl-2'-carboxycyclopropyl]glycine;
(2SR,1'RS,2'RS,3'RS)-2-[3'-trifluoromethyl-2'-carboxycyclopropyl]glycine;
(2SR,1'SR,2'SR,3'RS)-2-[3'-carboxymethyl-2'-carboxycyclopropyl]glycine;
(2SR,1'SR,2'SR,3'RS)-2-[(3'-(2''-(1H-tetrazol-5-yl)ethyl)-2'-carboxycyclopropyl]glycine;
(2SR,1'SR,2'SR,3'RS)-2-[(3'-(2''-carboxyethyl)-2'-carboxycyclopropyl]glycine;
(2SR,1'SR,2'SR,3'RS)-2-[(3'-(2''-azidoethyl)-2'-carboxycyclopropyl]glycine;
(2SR,1'SR,2'SR,3'RS)-2-[(3'-(2''-nitroethyl)-2'-carboxycyclopropyl]glycine;
(2SR,1'SR,2'SR,3'RS)-2-[3'-(5-phenyltetrazol-2-yl)methyl-2'-carboxycyclopropyl]glycine, and pharmaceutically acceptable salts and esters thereof.

9. (2S,1'S,2'R,3'R)-2-(3'-hydroxymethyl-2'-carboxycyclopropyl)glycine, or a pharmaceutically acceptable salt thereof.

10. A pharmaceutical formulation comprising a compound of formula I as claimed in any one of claims 1 to 3, 8 or 9, or a pharmaceutically acceptable metabolically labile ester thereof, or a pharmaceutically acceptable salt thereof, together with a pharmaceutically acceptable carrier, diluent or excipient.

11. A process for preparing a compound of formula I as claimed in any one of claims 1 to 3, 8 or 9, or a salt or ester thereof, which comprises:

(a) deprotecting a compound of formula

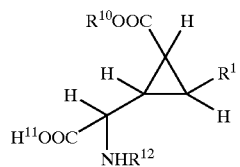

II in which $R^{10}$ and $R^{11}$ each independently represents hydrogen or a carboxyl protecting group, and $R^{12}$ represents hydrogen or an amine protecting group;

(b) hydrolysing a compound of formula

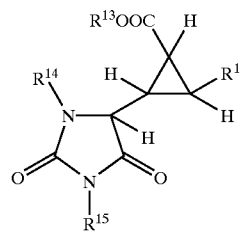

III in which $R^{13}$ represents a hydrogen atom or a carboxyl protecting group, and $R^{14}$ and $R^{15}$ each independently represents a hydrogen atom, a $C_{1-4}$ alkyl group or a phenyl $C_{1-4}$ alkyl group in which the phenyl group is unsubstituted or substituted by halo, $C_{1-4}$ alkyl, $C_{1-4}$ alkoxy or $C_{3-4}$ alkenyl; or (c) hydrolysing a compound of formula

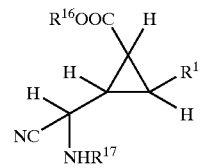

IV in which $R^{16}$ represents a hydrogen atom or a carboxy protecting group, and $R^{17}$ represents a hydrogen atom or an amine protecting group;

followed when necessary by recovering a diastereomer or isomer of the compound, or forming a salt or ester thereof.

12. A method of treating a patient suffering from or susceptible to a disorder of the central nervous system, which comprises administering an effective amount of a compound of formula I according to claim 1, or a pharmaceutically acceptable metabolically labile ester thereof, or a pharmaceutically acceptable salt thereof.

* * * * *